United States Patent
Wu et al.

(10) Patent No.: US 11,091,450 B2
(45) Date of Patent: Aug. 17, 2021

(54) CRYSTAL OF A CASPASE INHIBITOR

(71) Applicant: Chia Tai Tianqing Pharmaceutical Group Co., Ltd., Lianyungang (CN)

(72) Inventors: Songliang Wu, Shanghai (CN); Jianfeng Mou, Shanghai (CN); Haiying He, Shanghai (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 0 days.

(21) Appl. No.: 16/977,761

(22) PCT Filed: Mar. 13, 2019

(86) PCT No.: PCT/CN2019/077939
§ 371 (c)(1),
(2) Date: Sep. 2, 2020

(87) PCT Pub. No.: WO2019/174589
PCT Pub. Date: Sep. 19, 2019

(65) Prior Publication Data
US 2021/0002235 A1  Jan. 7, 2021

(30) Foreign Application Priority Data

Mar. 13, 2018 (CN) .......................... 201810206043.3
Jul. 20, 2018 (CN) .......................... 201810803581.0

(51) Int. Cl.
*C07D 261/18* (2006.01)
(52) U.S. Cl.
CPC ........ *C07D 261/18* (2013.01); *C07B 2200/13* (2013.01)

(58) Field of Classification Search
CPC .......................... C07D 261/18; C07B 2200/13
See application file for complete search history.

(56) References Cited

U.S. PATENT DOCUMENTS 10,981,860 B2 *  4/2021  He ....................... C07D 211/60

FOREIGN PATENT DOCUMENTS

| CN | 1313846 A | 9/2001 |
|---|---|---|
| CN | 1345332 A | 4/2002 |
| WO | WO 2018/133870 A1 | 7/2018 |

OTHER PUBLICATIONS

International Search Report for PCT/CN2019/077939 dated May 29, 2019.

* cited by examiner

*Primary Examiner* — Kamal A Saeed
(74) *Attorney, Agent, or Firm* — Knobbe Martens Olson & Bear LLP

(57) ABSTRACT

Disclosed herein a crystal structure of a caspase inhibitor, and more specifically a crystal structure of an (S)-3-((S)-2-(5-(2-chlorophenyl)isoxazole-3-formylamide)propona-mide)-4-oxo-5-(2,3,5,6-tetrafluorophenoxy)valeric acid, a preparation method therefor, a crystal polymer, a pharmaceutical composition and uses thereof. The compound A of formula (I) disclosed herein exhibits high crystal structure stability, low hygroscopicity, and advantageously shows physical properties, safety and metabolic stability while having relatively high pharmaceutical value.

19 Claims, 10 Drawing Sheets

CRYSTAL OF A CASPASE INHIBITOR

CROSS REFERENCE TO RELATED APPLICATIONS

This application is a U.S. National Phase Application of PCT International Application Number PCT/CN2019/077939, filed on Mar. 13, 2019, designating the United States of America and published in the Chinese language, which is an International Application of and claims the benefit of priority to Chinese Patent Application No. 201810206043.3, filed on Mar. 13, 2018, and Chinese Patent Application No. 201810803581.0, filed on Jul. 20, 2018. The disclosures of the above-referenced applications are hereby expressly incorporated by reference in their entireties.

TECHNICAL FIELD

The application belongs to the field of medicinal chemistry, relates to a crystal of a caspase inhibitor, more specifically relates to a crystal of (S)-3-((S)-2-(5-(2-chlorophenyl)isoxazol-3-carboxamido)propionamido)-4-oxo-5-(2,3,5,6-tetrafluorophenoxy)pentanoic acid, and a preparation method therefor, a pharmaceutical composition and uses thereof.

BACKGROUND

The control of the number of mammalian cell depends on the balance between reproduction and death of the cell to some extent. Necrotic cell death is one of the forms of cell death, characterized by pathological cell death caused by cell damage or injury. Necrotic cell death is harmful to tissues, such as, leading to inflammation. In contrast, another physiological form of cell death occurs in an orderly, controlled form. This orderly, controlled form of cell death is called as apoptotic cell death (Barr, et al., Bio/Technology, 12: 487-497, 1994; Steller, et al., 267: 1445-1449, 1995). Through this programmed manner of apoptotic cell death, an organism eliminates unwanted cells (activity and presence of the cells are no longer needed) without damaging other tissues. Therefore, apoptotic cell death is an extremely important physiological process to maintain the normal development and dynamic equilibrium of an organism.

There are many factors that can cause apoptotic cell death. Among them, the most important factor is a class of proteases called caspase (cysteine aspartate-specific protease, and 14 caspase proteases are known). Caspase is a type of cysteine protease, and many important proteins in cells are its substrate. The process of apoptotic cell death includes that cell debris formed by decomposing cells under the action of a caspase enzyme is absorbed by other cells, or eliminated by macrophages and the like without causing inflammation, etc.

SUMMARY OF THE INVENTION

In one aspect, the present application provides a crystal of a compound of formula I-A

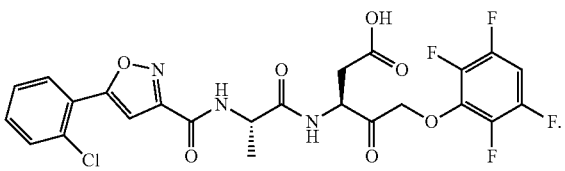

In another aspect, the present application provides a crystal composition of the compound of formula I-A, wherein the above crystal of the compound of formula I-A accounts for 50% or more, preferably 75% or more, more preferably 90% or more, and most preferably 95% or more by weight of the crystal composition.

In another aspect, the present application provides a pharmaceutical composition, comprising a therapeutically effective amount of the above crystal of the compound of formula I-A or the crystal composition of the compound of formula I-A as described above; said pharmaceutical composition may comprise at least one pharmaceutically acceptable carrier or other excipients.

In another aspect, the present application provides use of the above crystal of the compound of formula I-A, the above crystal composition of the compound of formula I-A, or the above pharmaceutical composition in the manufacture of a medicament for treating caspase receptor-related disease(s) in a mammal.

In another aspect, the present application provides a method for treating caspase receptor-related disease(s) in a mammal, comprising administering to the mammal in need thereof a therapeutically effective amount of the above crystal of the compound of formula I-A, the above crystal composition of the compound of formula I-A, or the above pharmaceutical composition.

In another aspect, the present application provides the above crystal of the compound of formula I-A, the above crystal composition of the compound of formula I-A, or the above pharmaceutical composition for use in treating caspase receptor-related diseases in a mammal.

DETAILED DESCRIPTION OF THE INVENTION

A compound has the structure represented by formula I-A, with the chemical name of: (S)-3-((S)-2-(5-(2-chlorophenyl)isoxazol-3-carboxamido)propionamido)-4-oxo-5-(2,3,5,6-tetrafluorophenoxy)pentanoic acid,

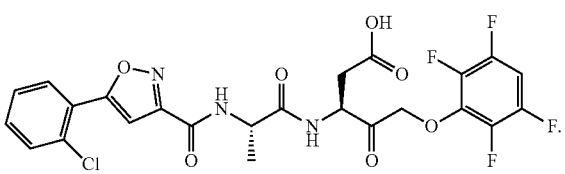

One aspect of the present application is to provide a crystal of the compound of formula I-A.

The crystal may be in the form of a non-solvate, or the form of a solvate such as a hydrate.

The crystal of the compound of formula I-A exhibits high stability, low hygroscopicity, and has a good metabolism level in vivo and a long half-life, also has good inhibitory activity on caspase enzyme, and has advantages in physical properties, safety and metabolic stability, with higher value as a medicament.

In some embodiments, the crystal of the compound of formula I-A of the present application is crystal I of the compound of formula I-A, characterized in that an X-ray powder diffraction spectrum represented by 2θ values has diffraction peaks at about 14.0°, 16.3°, 23.0°, and 25.7°; typically, the X-ray powder diffraction spectrum represented by 2θ values has diffraction peaks at about 9.6°, 14.0°, 14.5°, 15.0°, 16.3°, 23.0°, 25.1°, and 25.7°; more typically, the X-ray powder diffraction spectrum represented by 2θ values has diffraction peaks at about 4.7°, 7.4°, 9.6°, 14.0°, 14.5°, 15.0°, 16.3°, 17.1°, 20.9°, 21.7°, 22.5°, 23.0°, 24.5°, 25.1°, 25.7°, 28.1°, 32.0°, and 35.2°; more typically, the X-ray powder diffraction spectrum represented by 2θ values has diffraction peaks at about 4.7°, 7.4°, 7.9°, 9.6°, 14.0°, 14.5°, 15.0°, 16.3°, 17.1°, 19.8°, 20.4°, 20.9°, 21.7°, 22.5°, 23.0°, 24.5°, 25.1°, 25.7°, 28.1°, 30.0°, 32.0°, 34.1°, 35.2°, and 37.6°.

As an embodiment of the present application, the peak positions and intensities of the characteristic peaks in the X-ray powder diffraction spectrum of crystal I of the compound of formula I-A are shown in Table 1:

TABLE 1

XRPD spectrum characterization data of crystal I

| Number | Diffraction Angle 2θ (°) | Relative Intensity (%) |
| --- | --- | --- |
| 1 | 4.710 | 37.9 |
| 2 | 7.376 | 35.4 |
| 3 | 7.861 | 19.0 |
| 4 | 9.587 | 38.3 |
| 5 | 14.027 | 100 |
| 6 | 14.500 | 44.9 |
| 7 | 14.993 | 39.5 |
| 8 | 16.258 | 72.1 |
| 9 | 17.107 | 33.8 |
| 10 | 19.790 | 21.5 |
| 11 | 20.440 | 18.1 |
| 12 | 20.876 | 29.7 |
| 13 | 21.723 | 25.4 |
| 14 | 22.472 | 22.7 |
| 15 | 22.969 | 71.2 |
| 16 | 24.525 | 23.4 |
| 17 | 25.140 | 48.3 |
| 18 | 25.731 | 88.4 |
| 19 | 28.081 | 39.2 |
| 20 | 30.037 | 17.5 |
| 21 | 32.047 | 24.7 |
| 22 | 34.146 | 13.8 |
| 23 | 35.223 | 22.7 |
| 24 | 37.612 | 17.9 |

In an embodiment of the present application, the X-ray powder diffraction spectrum of crystal I of the compound of formula I-A is shown in FIG. 1.

In an embodiment of the present application, in a differential scanning calorimetry (DSC) measurement pattern of crystal I of the compound of formula I-A, onsets of absorption peaks are at about 120° C. and 153° C.

In an embodiment of the present application, the differential scanning calorimetry (DSC) measurement pattern of crystal I of the compound of formula I-A is shown in FIG. 2.

In an embodiment of the present application, the thermogravimetric analysis (TGA) pattern of crystal I of the compound of formula I-A is shown in FIG. 3.

In some embodiments, the crystal of the compound of formula I-A of the present application is crystal II of the compound of formula I-A, characterized in that an X-ray powder diffraction spectrum represented by 2θ values has diffraction peaks at about 8.5°, 14.2°, 15.8°, 17.1°, and 25.5°; typically, the X-ray powder diffraction spectrum represented by 2θ values has diffraction peaks at about 5.7°, 8.5°, 14.2°, 15.3°, 15.8°, 17.1°, 22.9°, 25.5°, 30.8°, and 33.3°; more typically, the X-ray powder diffraction spectrum represented by 2θ values has diffraction peaks at about 5.7°, 8.5°, 14.2°, 15.3°, 15.8°, 17.1°, 20.5°, 20.9°, 22.9°, 23.3°, 24.1°, 25.1°, 25.5°, 26.2°, 26.7°, 28.0°, 29.4°, 30.8°, 33.3°, 35.6°, and 37.1°.

As an embodiment of the present application, the peak positions and intensities of the characteristic peaks in the X-ray powder diffraction spectrum of crystal II of the compound of formula I-A are shown in Table 2:

TABLE 2

XRPD spectrum characterization data of crystal II

| Number | Diffraction Angle 2θ (°) | Relative Intensity (%) |
| --- | --- | --- |
| 1 | 5.695 | 9.0 |
| 2 | 8.463 | 40.2 |
| 3 | 14.243 | 56.3 |
| 4 | 15.309 | 10.6 |
| 5 | 15.824 | 100 |
| 6 | 17.068 | 81.5 |
| 7 | 20.459 | 4.8 |
| 8 | 20.915 | 5.4 |
| 9 | 22.929 | 14.3 |
| 10 | 23.340 | 7.6 |
| 11 | 24.134 | 6.3 |
| 12 | 25.060 | 8.7 |
| 13 | 25.475 | 43.5 |
| 14 | 26.191 | 4.4 |
| 15 | 26.740 | 8.1 |
| 16 | 28.044 | 4.3 |
| 17 | 29.422 | 7.5 |
| 18 | 30.805 | 13.0 |
| 19 | 33.313 | 13.3 |
| 20 | 35.620 | 4.0 |
| 21 | 37.062 | 4.8 |

In an embodiment of the present application, the X-ray powder diffraction pattern of crystal II of the compound of formula I-A is shown in FIG. 4.

In an embodiment of the present application, in a differential scanning calorimetry (DSC) measurement pattern of crystal II of the compound of formula I-A, an onset of absorption peak is at about 147° C.

In an embodiment of the present application, the differential scanning calorimetry (DSC) measurement pattern of crystal II of the compound of formula I-A is shown in FIG. 5.

In an embodiment of the present application, the thermogravimetric analysis (TGA) pattern of crystal II of the compound of formula I-A is shown in FIG. 6.

In some embodiments, the crystal of the compound of formula I-A of the present application is crystal IV of the compound of formula I-A, characterized in that an X-ray powder diffraction spectrum represented by 2θ values has diffraction peaks at about 11.2°, 15.1°, 15.6°, 16.7°, and 25.6°; typically, the X-ray powder diffraction spectrum represented by 2θ values has diffraction peaks at about 5.6°, 11.2°, 12.9°, 15.1°, 15.6°, 16.7°, 22.7°, and 25.6°; more typically, the X-ray powder diffraction spectrum represented by 2θ values has diffraction peaks at about 5.6°, 7.6°, 8.6°, 9.1°, 11.2°, 12.9°, 14.0°, 15.1°, 15.6°, 16.4°, 16.7°, 19.3°, 22.7°, 25.6°, 27.2°, 30.7°, 31.5°, 33.7°, and 34.7°; more typically, the X-ray powder diffraction spectrum represented by 2θ values has diffraction peaks at about 5.6°, 7.6°, 8.6°, 9.1°, 11.2°, 12.0°, 12.9°, 14.0°, 15.1°, 15.6°, 16.4°, 16.7°, 19.3°, 22.7°, 23.5°, 25.1°, 25.6°, 27.2°, 27.8°, 29.1°, 30.7°, 31.5°, 33.7°, 34.7°, 36.6°, 37.0°, and 38.2°.

As an embodiment of the present application, the peak positions and intensities of the characteristic peaks in the X-ray powder diffraction spectrum of crystal IV of the compound of formula I-A are shown in Table 3:

TABLE 3

| XRPD spectrum characterization data of crystal IV | | |
|---|---|---|
| Number | Diffraction Angle 2θ (°) | Relative Intensity (%) |
| 1 | 5.599 | 29.7 |
| 2 | 7.573 | 15.8 |
| 3 | 8.582 | 13.1 |
| 4 | 9.051 | 11.0 |
| 5 | 11.163 | 70.1 |
| 6 | 12.035 | 6.7 |
| 7 | 12.865 | 36.1 |
| 8 | 13.966 | 10.2 |
| 9 | 15.094 | 98.7 |
| 10 | 15.645 | 99.5 |
| 11 | 16.416 | 16.2 |
| 12 | 16.731 | 92.5 |
| 13 | 19.320 | 29.8 |
| 14 | 22.672 | 47.8 |
| 15 | 23.485 | 7.1 |
| 16 | 25.097 | 9.6 |
| 17 | 25.555 | 100 |
| 18 | 27.195 | 12.7 |
| 19 | 27.824 | 7.0 |
| 20 | 29.144 | 5.4 |
| 21 | 30.746 | 15.6 |
| 22 | 31.514 | 17.9 |
| 23 | 33.746 | 11.4 |
| 24 | 34.674 | 11.0 |
| 25 | 36.550 | 8.5 |
| 26 | 36.964 | 7.3 |
| 27 | 38.224 | 6.3 |

In an embodiment of the present application, the X-ray powder diffraction pattern of crystal IV of the compound of formula I-A is shown in FIG. 7.

In an embodiment of the present application, in a differential scanning calorimetry (DSC) measurement pattern of crystal IV of the compound of formula I-A, an onset of absorption peak is at about 167° C.

In an embodiment of the present application, the differential scanning calorimetry (DSC) measurement pattern of crystal IV of the compound of formula I-A is shown in FIG. 8.

In an embodiment of the present application, the thermogravimetric analysis (TGA) pattern of crystal IV of the compound of formula I-A is shown in FIG. 9.

In some embodiments, the crystal of the compound of formula I-A of the present application is crystal V of the compound of formula I-A, characterized in that an X-ray powder diffraction spectrum represented by 2θ values has diffraction peaks at about 6.9°, 8.3°, 13.9°, 15.7°, 16.9°, 25.3°, and 32.9°; typically, the X-ray powder diffraction spectrum represented by 2θ values has diffraction peaks at about 6.9°, 8.0°, 8.3°, 13.9°, 14.5°, 15.1°, 15.7°, 16.9°, 19.2°, 22.8°, 25.3°, and 32.9°.

As an embodiment of the present application, the peak positions and intensities of the characteristic peaks in the X-ray powder diffraction spectrum of crystal V of the compound of formula I-A are shown in Table 4:

TABLE 4

| XRPD spectrum characterization data of crystal V | | |
|---|---|---|
| Number | Diffraction Angle 2θ (°) | Relative Intensity (%) |
| 1 | 6.898 | 45.4 |
| 2 | 7.988 | 11.7 |
| 3 | 8.323 | 62.5 |
| 4 | 13.89 | 43.9 |
| 5 | 14.470 | 7.1 |
| 6 | 15.111 | 10.3 |
| 7 | 15.666 | 73.2 |
| 8 | 16.889 | 40.9 |
| 9 | 19.218 | 8.2 |
| 10 | 22.848 | 11.3 |
| 11 | 25.297 | 25.3 |
| 12 | 32.923 | 100 |

In an embodiment of the present application, the X-ray powder diffraction pattern of crystal V of the compound of formula I-A is shown in FIG. 10.

In an embodiment of the present application, in a differential scanning calorimetry (DSC) measurement pattern of crystal V of the compound of formula I-A, onsets of absorption peaks are at about 144° C. and 169° C.

In an embodiment of the present application, the differential scanning calorimetry (DSC) measurement pattern of crystal V of the compound of formula I-A is shown in FIG. 11.

In an embodiment of the present application, the thermogravimetric analysis (TGA) pattern of crystal V of the compound of formula I-A is shown in FIG. 12.

In some embodiments, the crystal of the compound of formula I-A of the present application is crystal VII of the compound of formula I-A, characterized in that the X-ray powder diffraction spectrum represented by 2θ values has diffraction peaks at about 6.9°, 7.6°, 8.3°, 9.6°, 13.9°, 15.2°, 16.4°, and 16.8°; typically, the X-ray powder diffraction spectrum represented by 2θ values has diffraction peaks at about 6.9°, 7.6°, 8.3°, 9.6°, 12.4°, 12.7°, 13.9°, 14.6°, 15.2°, 16.4°, 16.8°, 19.2°, 20.5°, 21.9°, 22.3°, 23.1°, 24.8°, 25.6°, 30.5°, 30.9°, and 32.1°.

As an embodiment of the present application, the peak positions and intensities of the characteristic peaks in the X-ray powder diffraction spectrum of crystal VII of the compound of formula I-A are shown in Table 5:

TABLE 5

| XRPD spectrum characterization data of crystal VII | | |
|---|---|---|
| Number | Diffraction Angle 2θ (°) | Relative Intensity (%) |
| 1 | 6.923 | 17.5 |
| 2 | 7.592 | 20.4 |
| 3 | 8.296 | 13.3 |
| 4 | 9.571 | 27.7 |
| 5 | 12.425 | 15.5 |
| 6 | 12.682 | 10.0 |
| 7 | 13.866 | 20.0 |
| 8 | 14.594 | 11.4 |
| 9 | 15.172 | 68.9 |
| 10 | 16.437 | 19.0 |
| 11 | 16.847 | 100 |
| 12 | 19.238 | 12.3 |
| 13 | 20.496 | 6.0 |
| 14 | 21.946 | 10.1 |
| 15 | 22.297 | 8.8 |
| 16 | 23.087 | 6.4 |

TABLE 5-continued

XRPD spectrum characterization data of crystal VII

| Number | Diffraction Angle 2θ (°) | Relative Intensity (%) |
|---|---|---|
| 17 | 24.805 | 8.8 |
| 18 | 25.595 | 8.0 |
| 19 | 30.546 | 3.6 |
| 20 | 30.907 | 5.6 |
| 21 | 32.105 | 4.3 |

In an embodiment of the present application, the X-ray powder diffraction pattern of crystal VII of the compound of formula I-A is shown in FIG. 13.

In an embodiment of the present application, in a differential scanning calorimetry (DSC) measurement pattern of crystal VII of the compound of formula I-A, an onset of absorption peak is at about 172° C.

In an embodiment of the present application, the differential scanning calorimetry (DSC) measurement pattern of crystal VII of the compound of formula I-A is shown in FIG. 14.

In an embodiment of the present application, the thermogravimetric analysis (TGA) pattern of crystal VII of the compound of formula I-A is shown in FIG. 15.

In some embodiments, the crystal of the compound of formula I-A of the present application is crystal VIII of the compound of formula I-A, characterized in that the X-ray powder diffraction spectrum represented by 2θ values has diffraction peaks at about 7.0°, 8.1°, 14.0°, 16.2°, and 19.3°; typically, the X-ray powder diffraction spectrum represented by 2θ values has diffraction peaks at about 7.0°, 8.1°, 14.0°, 14.6°, 16.2°, 16.6°, 17.6°, 19.3°, 22.9°, 25.4°, and 26.6°; more typically, the X-ray powder diffraction spectrum represented by 2θ values has diffraction peaks at about 7.0°, 8.1°, 8.4°, 13.3°, 14.0°, 14.6°, 15.8°, 16.2°, 16.6°, 17.0°, 17.6°, 19.3°, 20.6°, 21.5°, 22.9°, 24.6°, 25.4°, 26.6°, 28.2°, 29.4°, 30.2°, 30.8°, 32.1°, 34.4°, and 38.4°.

As an embodiment of the present application, the peak positions and intensities of the characteristic peaks in the X-ray powder diffraction spectrum of crystal VIII of the compound of formula I-A are shown in Table 6:

TABLE 6

XRPD spectrum characterization data of crystal VIII

| Number | Diffraction Angle 2θ (°) | Relative Intensity (%) |
|---|---|---|
| 1 | 7.019 | 54.0 |
| 2 | 8.089 | 34.6 |
| 3 | 8.423 | 9.2 |
| 4 | 13.291 | 8.8 |
| 5 | 14.026 | 100 |
| 6 | 14.597 | 21.4 |
| 7 | 15.789 | 8.4 |
| 8 | 16.178 | 39.9 |
| 9 | 16.554 | 10.0 |
| 10 | 17.025 | 8.6 |
| 11 | 17.642 | 26.5 |
| 12 | 19.335 | 38.4 |
| 13 | 20.565 | 7.4 |
| 14 | 21.451 | 7.6 |
| 15 | 22.870 | 13.6 |
| 16 | 24.608 | 9.0 |
| 17 | 25.378 | 13.3 |
| 18 | 26.597 | 23.3 |
| 19 | 28.197 | 8.1 |
| 20 | 29.401 | 5.0 |
| 21 | 30.168 | 4.2 |
| 22 | 30.786 | 4.0 |
| 23 | 32.067 | 8.2 |

TABLE 6-continued

XRPD spectrum characterization data of crystal VIII

| Number | Diffraction Angle 2θ (°) | Relative Intensity (%) |
|---|---|---|
| 24 | 34.359 | 3.6 |
| 25 | 38.443 | 4.1 |

In an embodiment of the present application, the X-ray powder diffraction pattern of crystal VIII of the compound of formula I-A is shown in FIG. 16.

In an embodiment of the present application, in a differential scanning calorimetry (DSC) measurement pattern of crystal VIII of the compound of formula I-A, onsets of absorption peaks are at about 152° C. and 171° C.

In an embodiment of the present application, the differential scanning calorimetry (DSC) measurement pattern of crystal VIII of the compound of formula I-A is shown in FIG. 17.

In some embodiments, the crystal of the compound of formula I-A of the present application is crystal IX of the compound of formula I-A, characterized in that the X-ray powder diffraction spectrum represented by 2θ values has diffraction peaks at about 4.6°, 9.4°, 13.8°, 16.1°, 16.9°, and 25.6°; typically, the X-ray powder diffraction spectrum represented by 2θ values has diffraction peaks at about 4.6°, 7.2°, 9.0°, 9.4°, 13.8°, 14.3°, 14.8°, 16.1°, 16.9°, and 25.6°; more typically, the X-ray powder diffraction spectrum represented by 2θ values has diffraction peaks at about 4.6°, 7.2°, 9.0°, 9.4°, 12.9°, 13.8°, 14.3°, 14.8°, 16.1°, 16.9°, 17.7°, 21.5°, 22.2°, 23.2°, 25.6°, and 31.8°.

As an embodiment of the present application, the peak positions and intensities of the characteristic peaks in the X-ray powder diffraction spectrum of crystal IX of the compound of formula I-A are shown in Table 7:

TABLE 7

XRPD spectrum characterization data of crystal IX

| Number | Diffraction Angle 2θ (°) | Relative Intensity (%) |
|---|---|---|
| 1 | 4.551 | 100 |
| 2 | 7.157 | 22.3 |
| 3 | 9.037 | 15.1 |
| 4 | 9.393 | 49.7 |
| 5 | 12.923 | 9.9 |
| 6 | 13.829 | 66.8 |
| 7 | 14.304 | 28.2 |
| 8 | 14.781 | 27.9 |
| 9 | 16.099 | 61.3 |
| 10 | 16.931 | 44.1 |
| 11 | 17.658 | 15.4 |
| 12 | 21.509 | 11.9 |
| 13 | 22.238 | 14.4 |
| 14 | 23.164 | 14.4 |
| 15 | 25.593 | 52.5 |
| 16 | 31.812 | 8.5 |

In an embodiment of the present application, the X-ray powder diffraction pattern of crystal IX of the compound of formula I-A is shown in FIG. 18.

In an embodiment of the present application, in a differential scanning calorimetry (DSC) measurement pattern of crystal IX of the compound of formula I-A, an onset of absorption peak is at about 170° C.

In an embodiment of the present application, the differential scanning calorimetry (DSC) measurement pattern of crystal IX of the compound of formula I-A is shown in FIG. 19.

In another aspect, the present application provides a method for preparing crystal I of the compound of formula I-A, comprising: (1) adding a crude of the compound of formula I-A into a solvent, sonicating, and precipitating as a solid; (2) adding the same solvent as step (1), stirring and filtering; (3) adding the resultant filter cake into the same solvent as step (1), stirring and filtering to obtain crystal I of the compound of formula I-A; wherein, the solvent in the above steps (1), (2) and (3) is selected from methanol, ethanol, isopropanol, acetone, acetonitrile, tetrahydrofuran, ethylene glycol, propylene glycol, water or a mixed solvent of water and the above solvent(s).

In an embodiment of the present application, the solvent in the above steps (1), (2) and (3) is selected from acetonitrile or water.

In another aspect, the present application provides a method for preparing crystal IV of the compound of formula I-A, comprising:
(1) adding the compound of formula I-A or crystal I of the compound of formula I-A into a solvent, to form a suspension or solution;
(2) heating and stirring the above suspension or solution in a magnetic stirrer, centrifuging or filtering to obtain crystal IV of the compound of formula I-A;
wherein, the solvent in the above step (1) is selected from a mixed solvent of acetone and water.

In an embodiment of the present application, in the above-mentioned mixed solvent of acetone and water, the volume ratio of acetone to water is 1:2.

In an embodiment of the present application, in the above step (1), the molar volume ratio of the compound of formula I-A or crystal I of the compound of formula I-A to the solvent is (0.01-0.1 mmol):1 mL; preferably, (0.02-0.08 mmol):1 mL; more preferably, (0.03-0.07 mmol):1 mL.

In an embodiment of the present application, the stirring described in the above step (2) is performed at 20-50° C.; preferably, 30-50° C.; more preferably, 40-50° C.

In an embodiment of the present application, a time of the stirring described in the above step (2) is 12-48 hours; preferably, 16-48 hours.

The crude of the compound of formula I-A in the present application contains a compound of formula I-B as an enantiomer, and the compound of formula I-B accounts for 0.1%-15% of the total weight of the crude of the compound of formula I-A, wherein the structural formula of the compound of formula I-B is shown as follows:

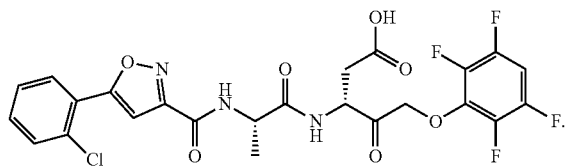

I-B

During the preparation process of the crystal of the compound of formula I-A of the present application, the compound of formula I-B as the enantiomer can also be converted into its crystal form(s), and the crystal of the compound of formula I-B accounts for 0.1% to 15% of the total weight of the crystal.

In another aspect, the present application provides a crystal composition of the compound of formula I-A, wherein the above crystal of the compound of formula I-A accounts for 50% or more, preferably 75% or more, more preferably 90% or more, and most preferably 95% or more by weight of the crystal composition. The crystal composition may also contain a small amount of other crystals or an amorphous form of the compound of formula I-A or a crystal of the compound of formula I-B.

In another aspect, the present application provides a pharmaceutical composition, comprising a therapeutically effective amount of the above crystal of the compound of formula I-A or the above crystal composition of the compound of formula I-A; said pharmaceutical composition may comprise at least one pharmaceutically acceptable carrier or other excipients.

In another aspect, the present application provides use of the above crystal of the compound of formula I-A, the above crystal composition of the compound of formula I-A, or the above pharmaceutical composition in the manufacture of a medicament for treating caspase receptor-disease(s) in a mammal.

In another aspect, the present application provides a method for treating caspase receptor-related disease(s) in a mammal, comprising administering to the mammal in need thereof a therapeutically effective amount of the above crystal of the compound of formula I-A, the above crystal composition of the compound of formula I-A, or the above pharmaceutical composition.

In another aspect, the present application provides the above crystal of the compound of formula I-A, the above crystal composition of the compound of formula I-A, or the above pharmaceutical composition for use in treating caspase receptor-related disease(s) in a mammal.

In some embodiments of the present application, the mammal is human.

In the present application, the pharmaceutical composition can be prepared into a certain dosage form, and the route of administration is preferably oral administration, parenteral (including subcutaneous, intramuscular and intravenous) administration, rectal administration and the like. For example, dosage forms suitable for oral administration include tablet, capsule, granule, pulvis, pill, powder, lozenge, syrup or suspension; dosage forms suitable for parenteral administration include aqueous or non-aqueous solution for injection or emulsion; dosage forms suitable for rectal administration include suppository using hydrophilic or hydrophobic carriers. According to needs, the above dosage forms can also be prepared into dosage forms suitable for rapid release, delayed release or controlled release of active ingredients.

In some embodiments of the present application, said caspase receptor-related disease in a mammal is selected from nonalcoholic fatty liver disease, hepatitis or liver fibrosis.

In the present application, the X-ray powder diffraction spectrums of samples are determined under the following conditions: Instrument: Bruker D8 ADVANCE X-ray diffractometer; Target: Cu: Kα; Wavelength λ=1.54179 Å; 2θ angle range: 4-40°; Scanning speed: 10°/min; Sample rotation speed: 15 rpm; Tube voltage and tube current of Cu Target: 40 kV, 40 mA.

In the present application, a DSC pattern is determined under the following conditions: Instrument: TA Q2000 differential scanning calorimeter; Temperature range: 25-300° C.; Heating rate: 10° C./min.

In the present application, a TGA pattern is determined under the following conditions: Instrument: TA Q 5000 thermogravimetric analyzer; Temperature range: 25-300° C.; Heating rate: 10° C./min.

It should be noted that, in an X-ray diffraction spectrum, a diffraction pattern obtained from a crystal compound is usually characteristic for a specific crystal. Relative intensities of bands (especially at low angles) in the diffraction pattern may vary depending upon preferential orientation effects resulting from the differences of crystallization conditions, particle sizes, and other measuring conditions. Therefore, the relative intensities of diffraction peaks are not characteristic for the targeted crystalline form. It is the relative positions of peaks rather than relative intensities thereof that should be paid more attention when judging whether a crystalline form is the same as a known crystalline form. In addition, as for any given crystalline form, there may be a slight error in the positions of peaks, which is also well known in the field of crystallography. For example, the position of a peak may shift due to the change of a temperature, the movement of a sample or the calibration of an instrument and so on when analyzing the sample, and the measurement error of 2θ value is sometimes about ±0.2°. Accordingly, this error should be taken into consideration when identifying a crystal structure. Usually, the position of a peak is expressed in terms of 2θ angle or interplanar spacing d in an XRD pattern and the simple conversion relationship therebetween is d=λ/2 sin θ, wherein d represents the interplanar spacing, λ, represents the wavelength of incident X-ray, and θ represents the diffraction angle. For the same crystal of the same compound, the positions of peaks in an XRD spectrum thereof have similarity on the whole, and the error of relative intensities may be larger. It is also should be pointed out that due to some factors such as reduced contents, parts of diffraction lines may be absent in the identification of a mixture. At this time, even one band may be characteristic for the given crystal without depending upon all the bands observed in a high purity sample.

DSC is used to measure a transition temperature when a crystal absorbs or releases heat due to the change of the crystal structure thereof or the melting of the crystal. During a continuous analysis of the same crystalline form of the same compound, the error of a thermal transition temperature and a melting point is typically within a range of about 5° C., usually about 3° C., or about 2° C. When it is said that a compound has a given DSC peak or melting point, it means that the DSC peak or melting point may be varied within a range of ±5° C. DSC provides an auxiliary method to distinguish different crystalline forms. Different crystalline forms can be identified by their characteristically different transition temperatures. It should be pointed out that, for a mixture, the DSC peak or melting point may be varied in a larger range. In addition, the melting temperature is related to the heating rate because the melting process is accompanied by decomposition.

Definitions and Description

When used in the description and claims of the present application, unless otherwise specified, the following terms are intended to have the following meanings:

"Mammal" includes human; domestic animal, such as laboratory mammal and domestic pet (such as cat, dog, pig, caprinae, cattle, sheep, goat, horse, rabbit), and non-domesticated mammal such as wild mammal.

The term "pharmaceutical composition" refers to a preparation of a compound of the present application and a medium generally accepted in the art for delivering a biologically active compound to a mammal such as human. The medium includes all pharmaceutically acceptable carriers for its use. The pharmaceutical composition facilitates the administration of a compound to an organism.

The term "therapeutically effective amount" refers to an amount of a drug or formulation that is sufficient to be able to achieve desired effects but non-toxic. The determination of an effective amount varies from person to person, depending on the age and the general condition of a subject, and also depending on the specific active substance. An appropriate effective amount in individual cases can be determined by the person skilled in the art according to conventional tests.

In the present application, "pharmaceutically acceptable carrier" refers to those carriers that are administered together with the active substance, have no obvious irritation effect on the organism, and do not impair the biological activity and performance of the active substance. Other information about carriers can refer to Remington: The Science and Practice of Pharmacy, 21st Ed., Lippincott, Williams & Wilkins (2005), the contents of which are incorporated herein by reference.

In the present application, "room temperature" refers to 20-25° C.

DETAILED DESCRIPTION

Figure 1:
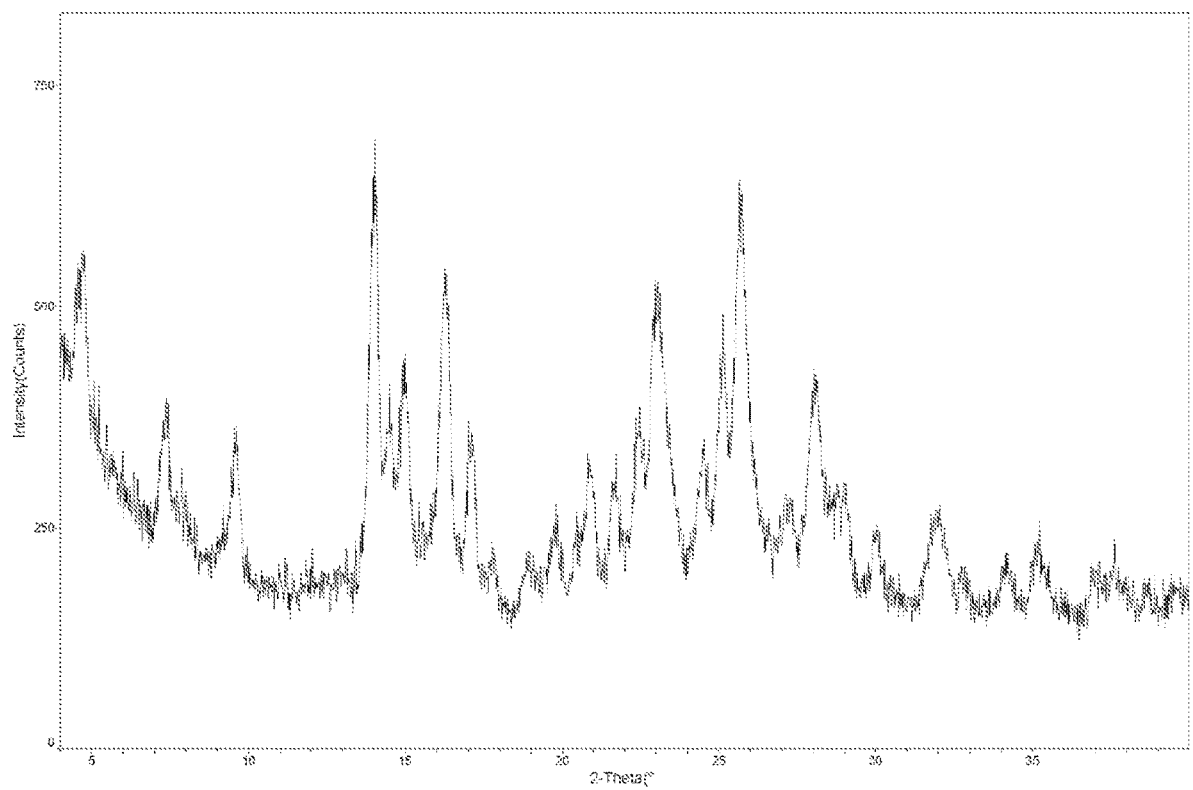
FIG. 1 is an X-ray powder diffraction (XRPD) pattern of crystal I of the compound of formula I-A of Example 2.
Figure 2:
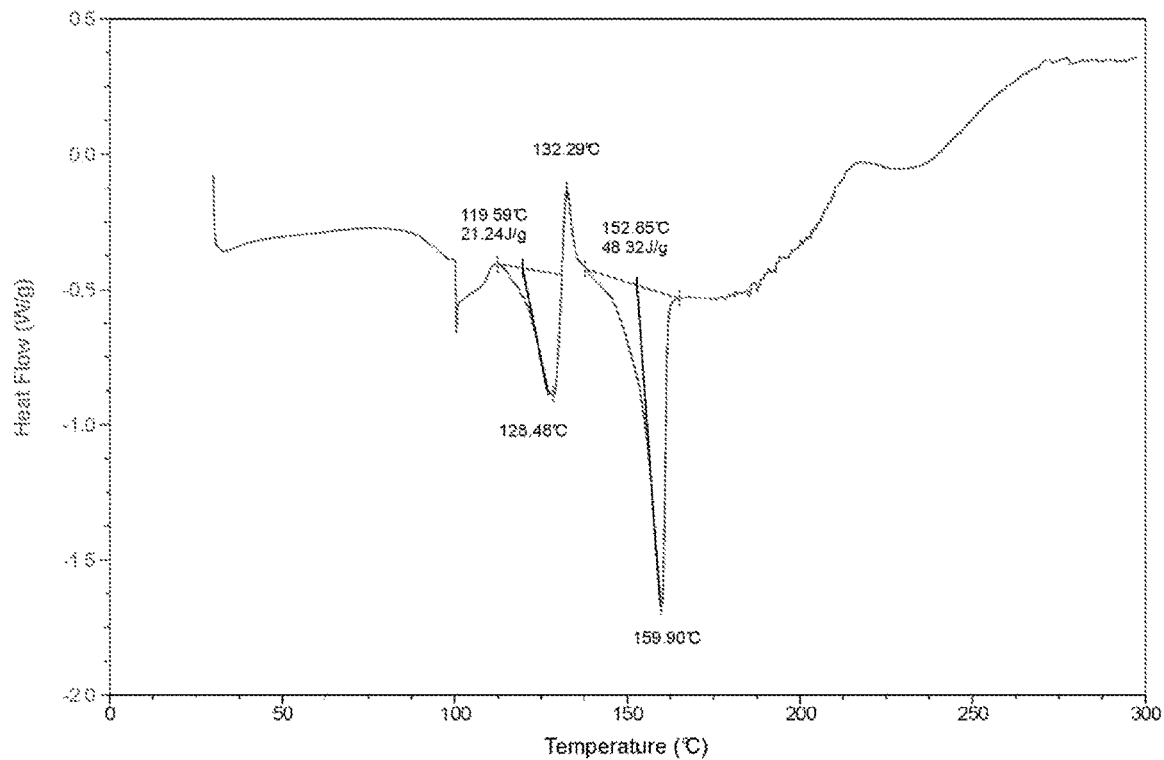
FIG. 2 is a differential scanning calorimetry (DSC) pattern of crystal I of the compound of formula I-A of Example 2.
Figure 3:
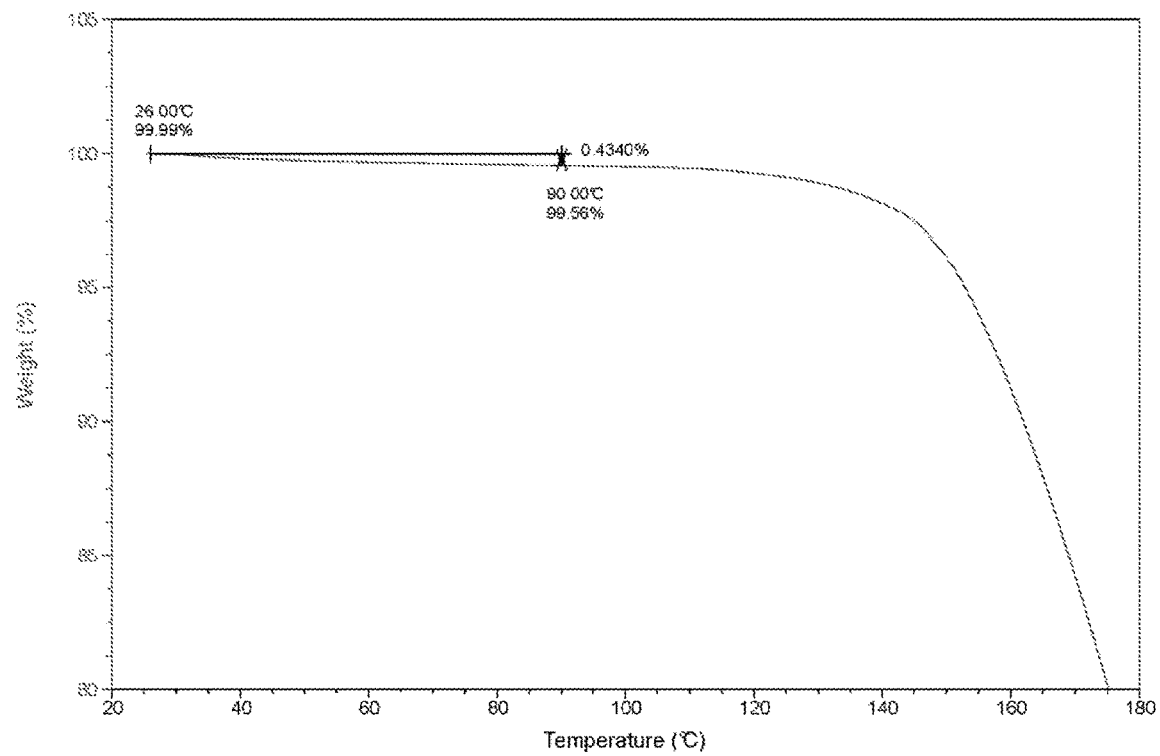
FIG. 3 is a thermogravimetric analysis (TGA) pattern of crystal I of the compound of formula I-A of Example 2.
Figure 4:
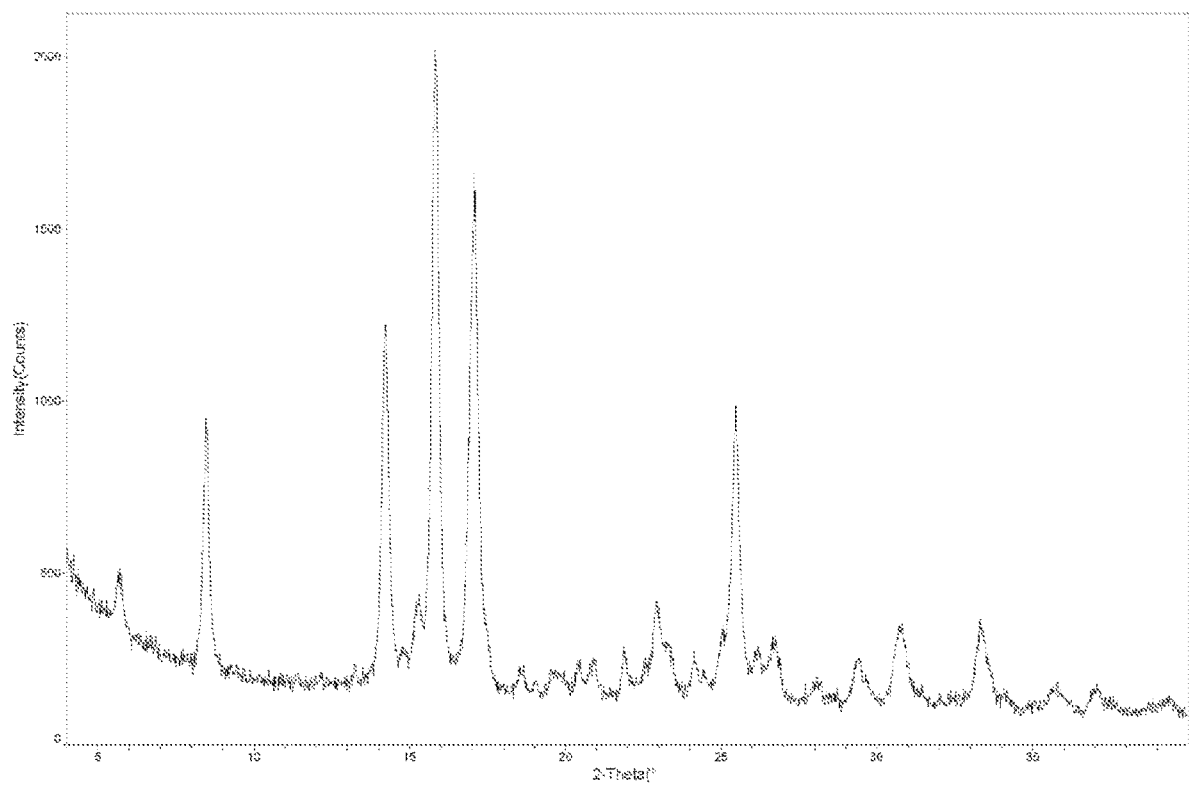
FIG. 4 is an X-ray powder diffraction (XRPD) pattern of crystal II of the compound of formula I-A of Example 3.
Figure 5:
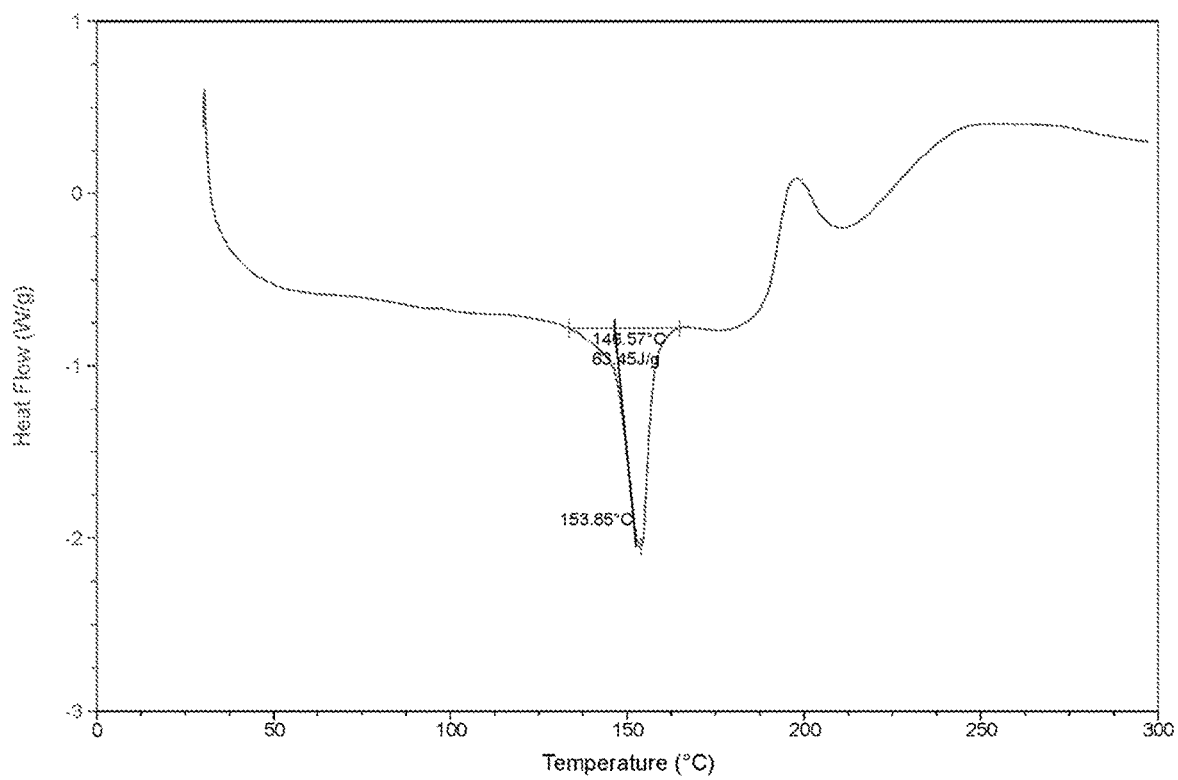
FIG. 5 is a differential scanning calorimetry (DSC) pattern of crystal II of the compound of formula I-A of Example 3.
Figure 6:
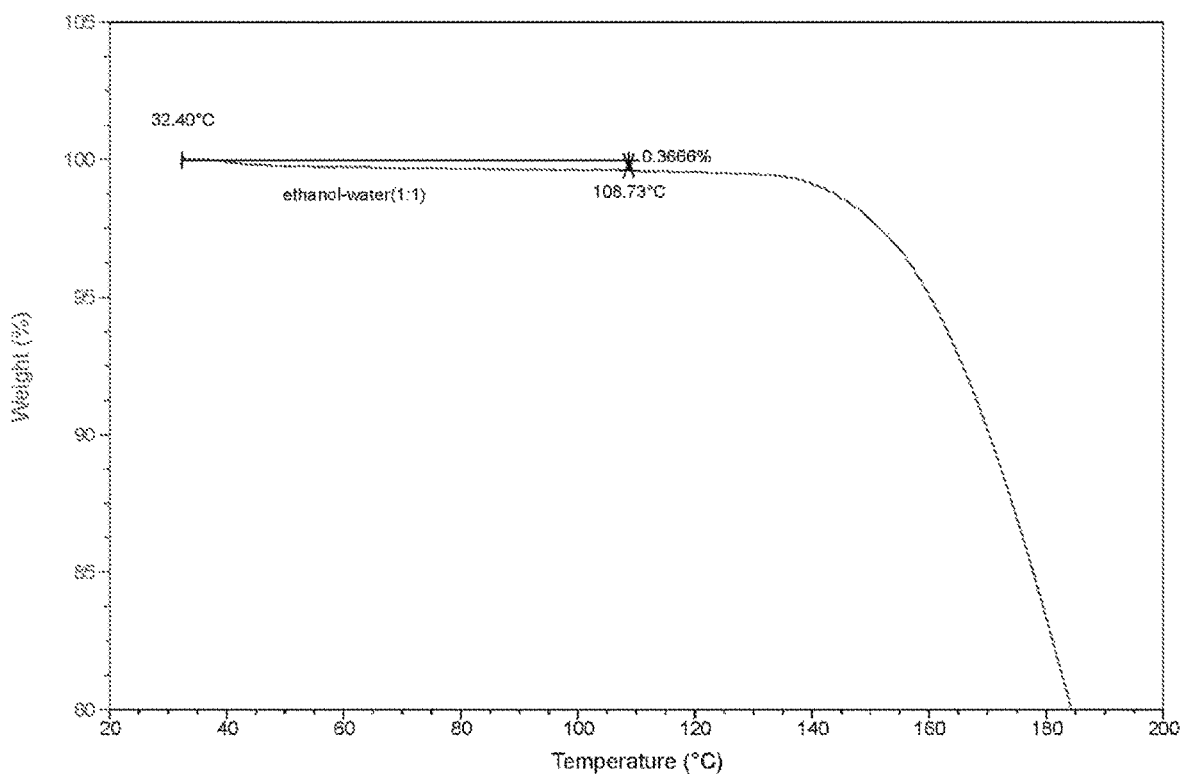
FIG. 6 is a thermogravimetric analysis (TGA) pattern of crystal II of the compound of formula I-A of Example 3.
Figure 7:
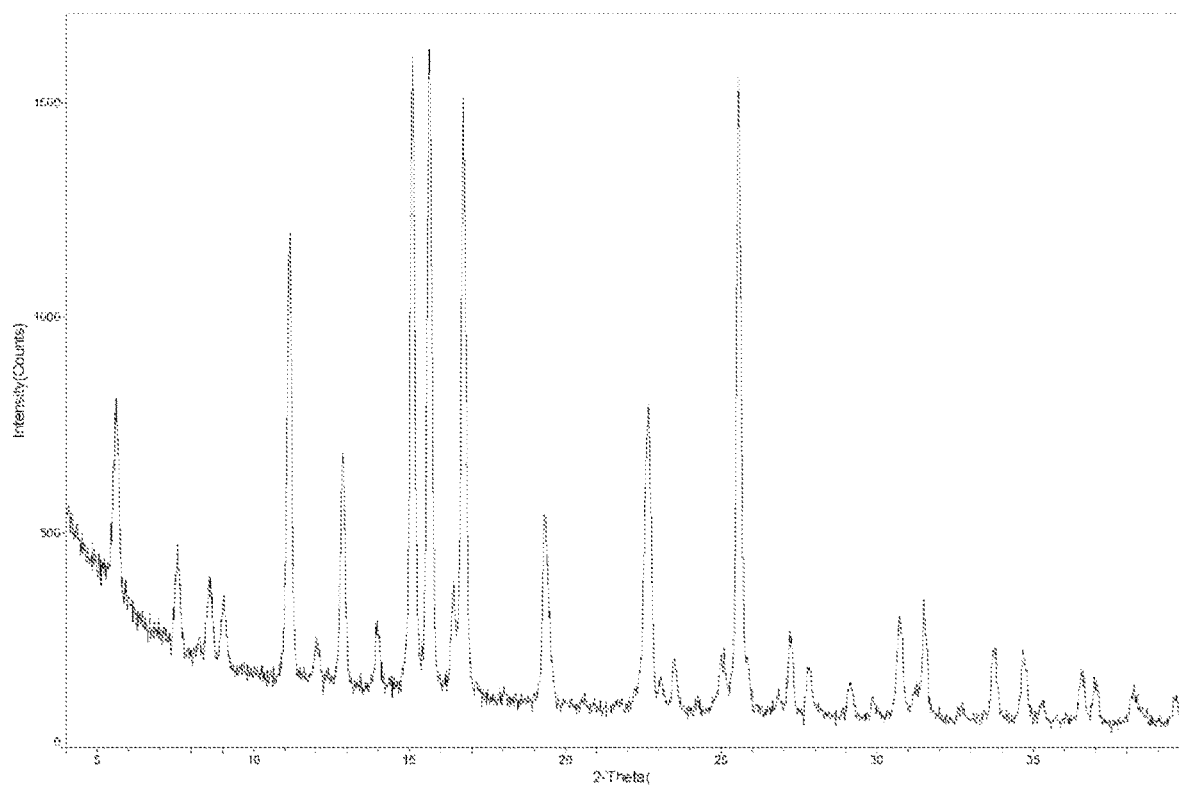
FIG. 7 is an X-ray powder diffraction (XRPD) pattern of crystal IV of the compound of formula I-A of Example 5.
Figure 8:
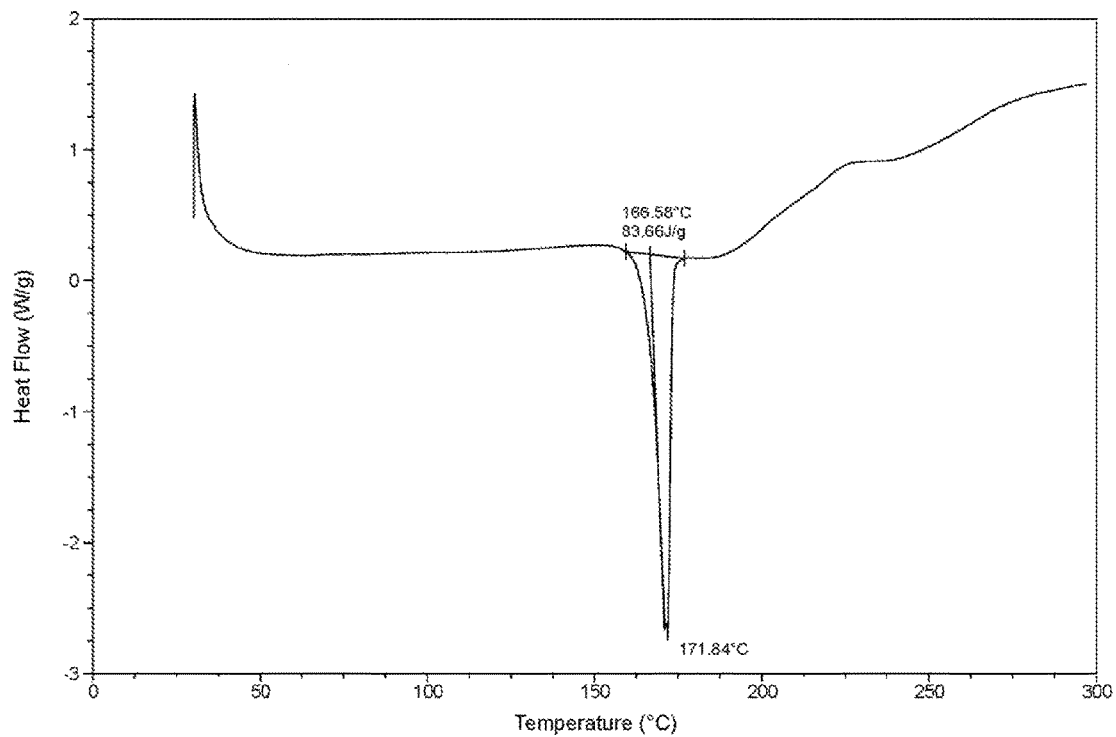
FIG. 8 is a differential scanning calorimetry (DSC) pattern of crystal IV of the compound of formula I-A of Example 5.
Figure 9:
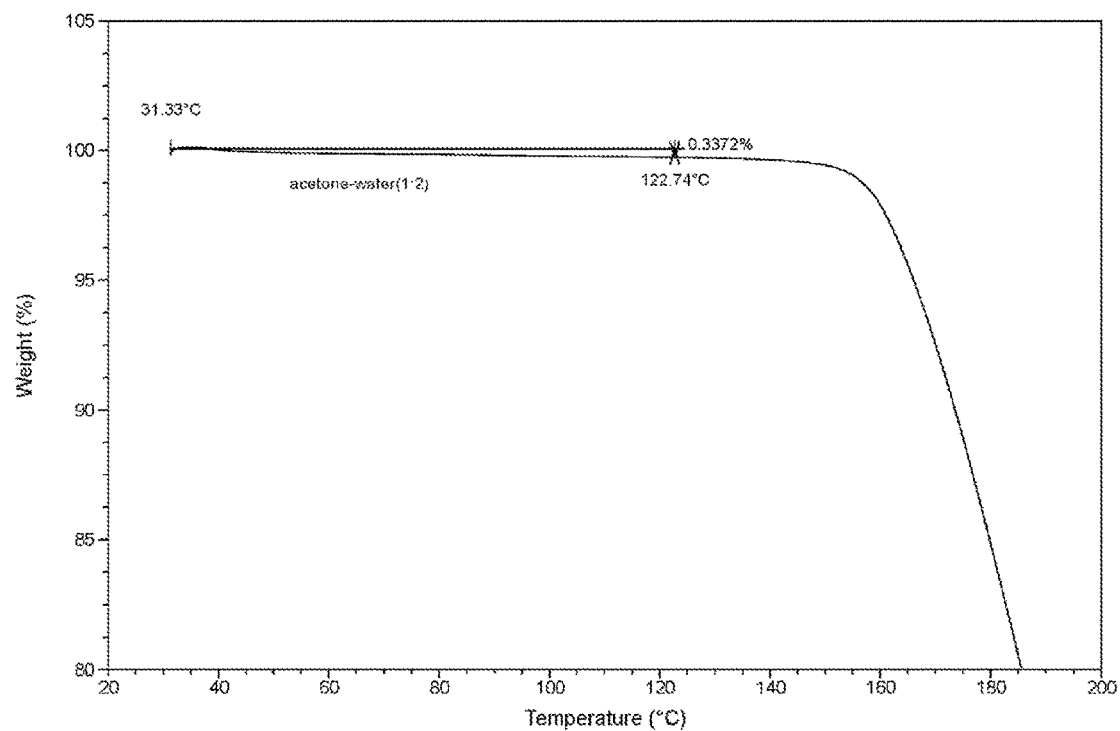
FIG. 9 is a thermogravimetric analysis (TGA) pattern of crystal IV of the compound of formula I-A of Example 5.
Figure 10:
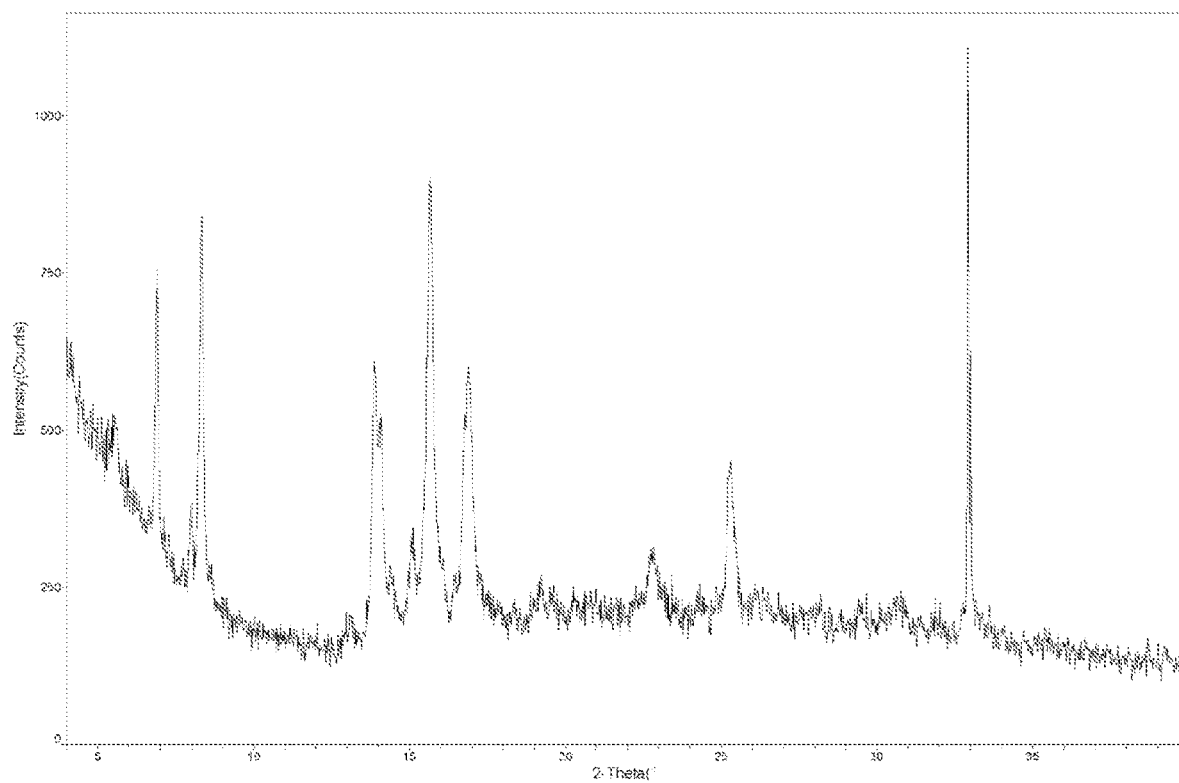
FIG. 10 is an X-ray powder diffraction (XRPD) pattern of crystal V of the compound of formula I-A of Example 7.
Figure 11:
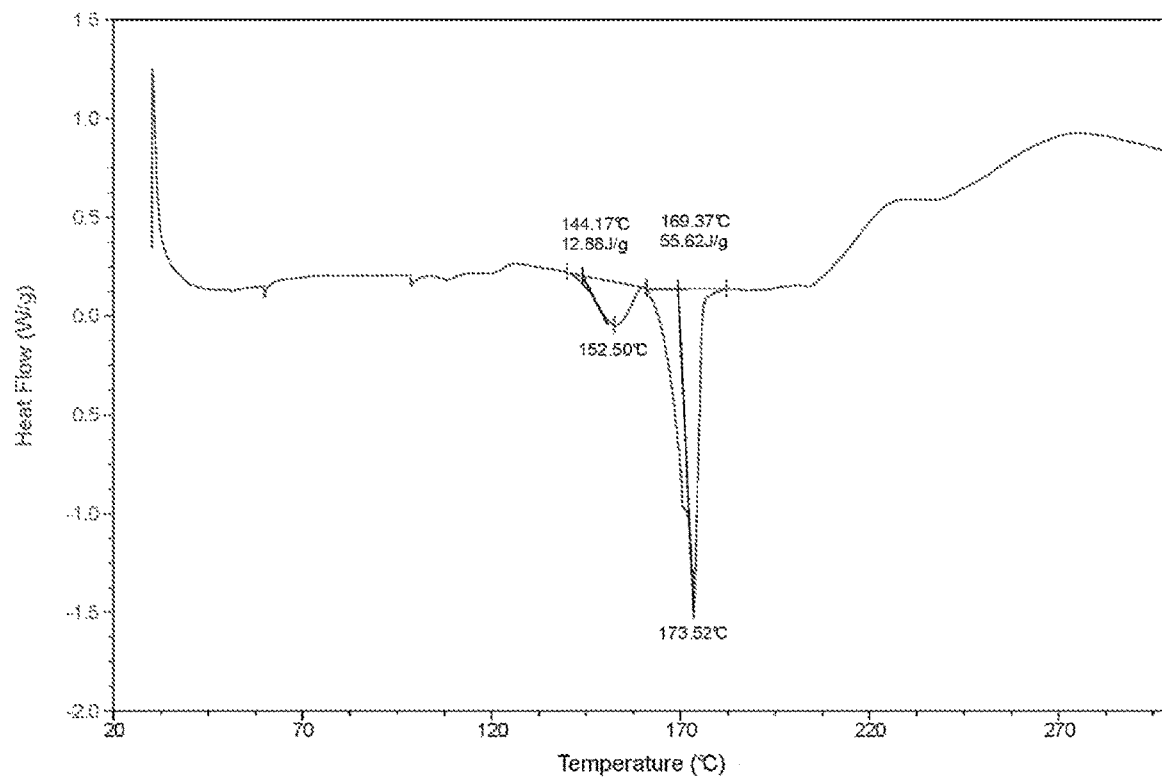
FIG. 11 is a differential scanning calorimetry (DSC) pattern of crystal V of the compound of formula I-A of Example 7.
Figure 12:
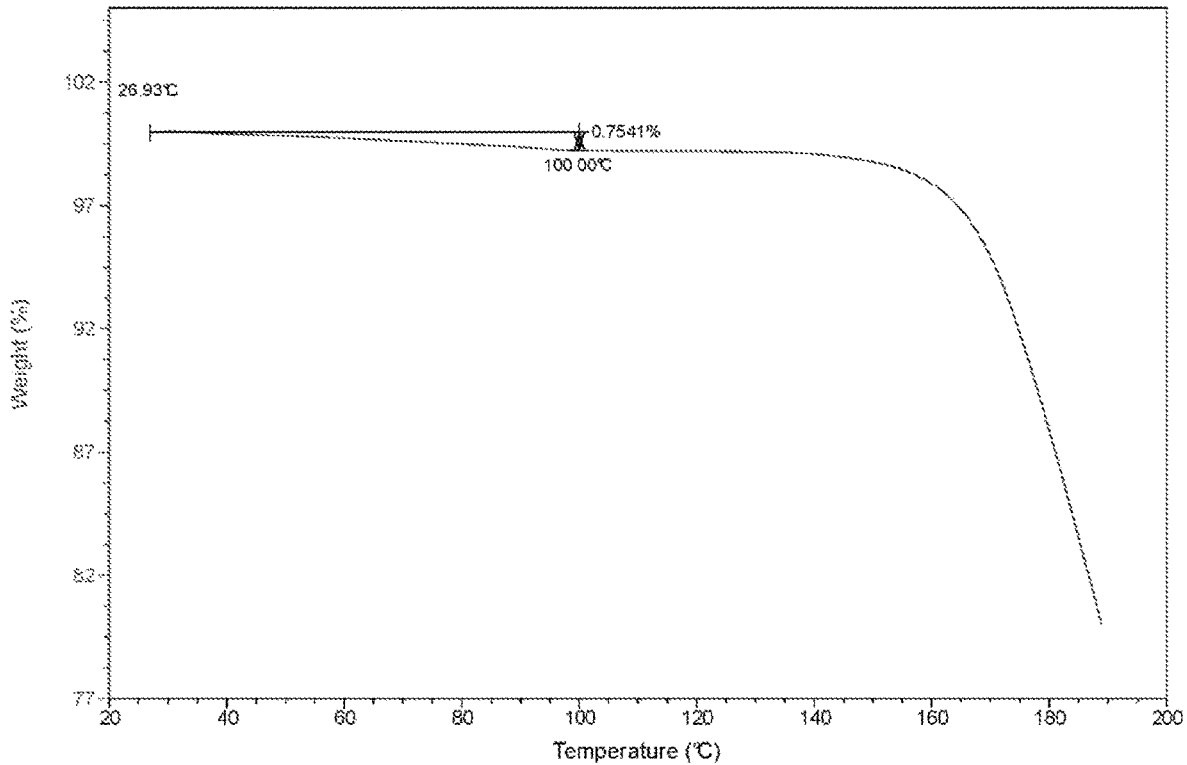
FIG. 12 is a thermogravimetric analysis (TGA) pattern of crystal V of the compound of formula I-A of Example 7.
Figure 13:
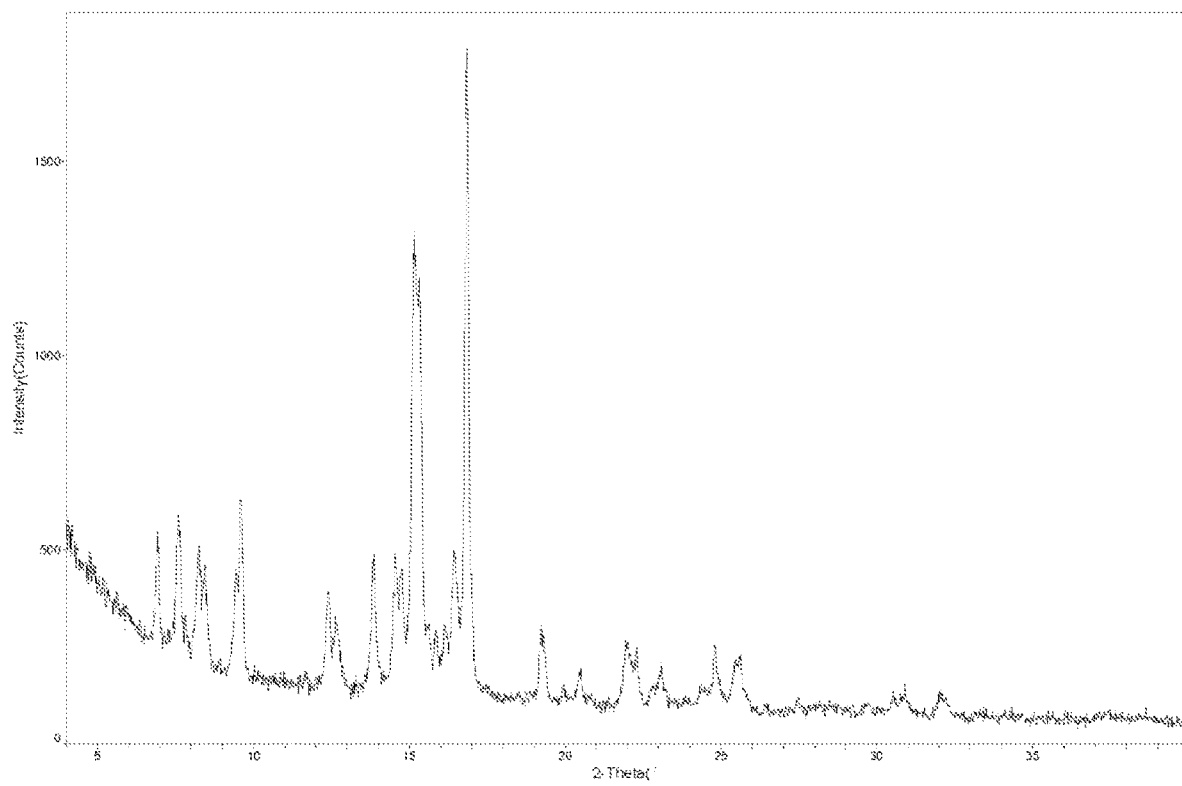
FIG. 13 is an X-ray powder diffraction (XRPD) pattern of crystal VII of the compound of formula I-A of Example 8.
Figure 14:
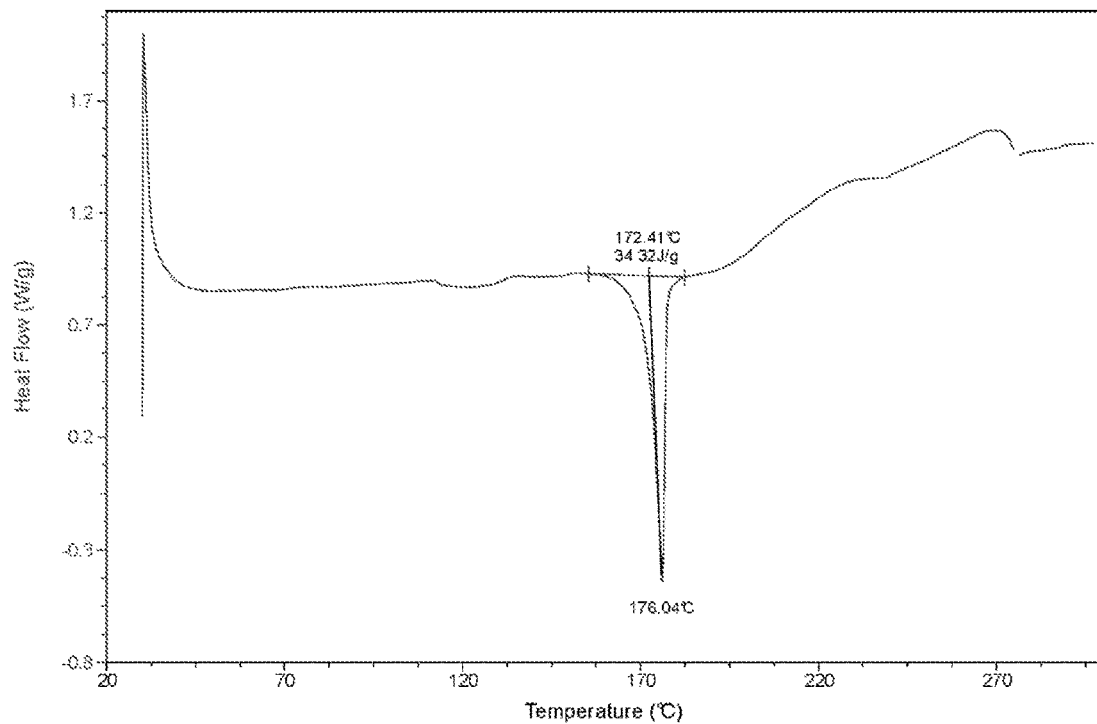
FIG. 14 is a differential scanning calorimetry (DSC) pattern of crystal VII of the compound of formula I-A of Example 8.
Figure 15:
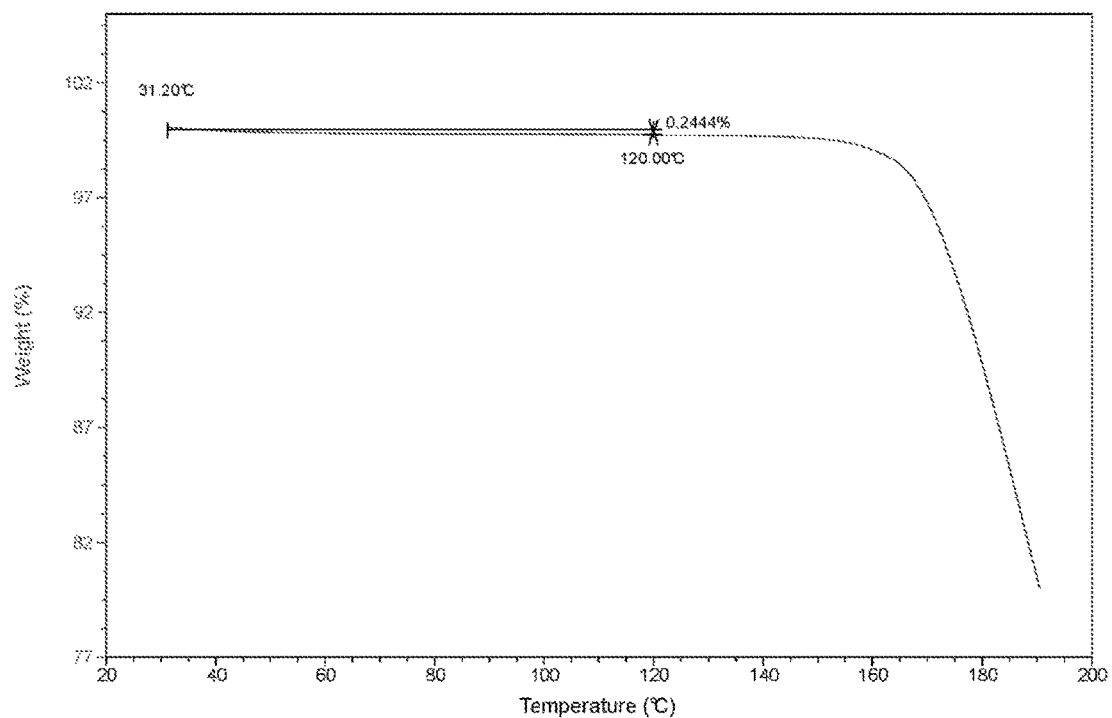
FIG. 15 is a thermogravimetric analysis (TGA) pattern of crystal VII of the compound of formula I-A of Example 8.
Figure 16:
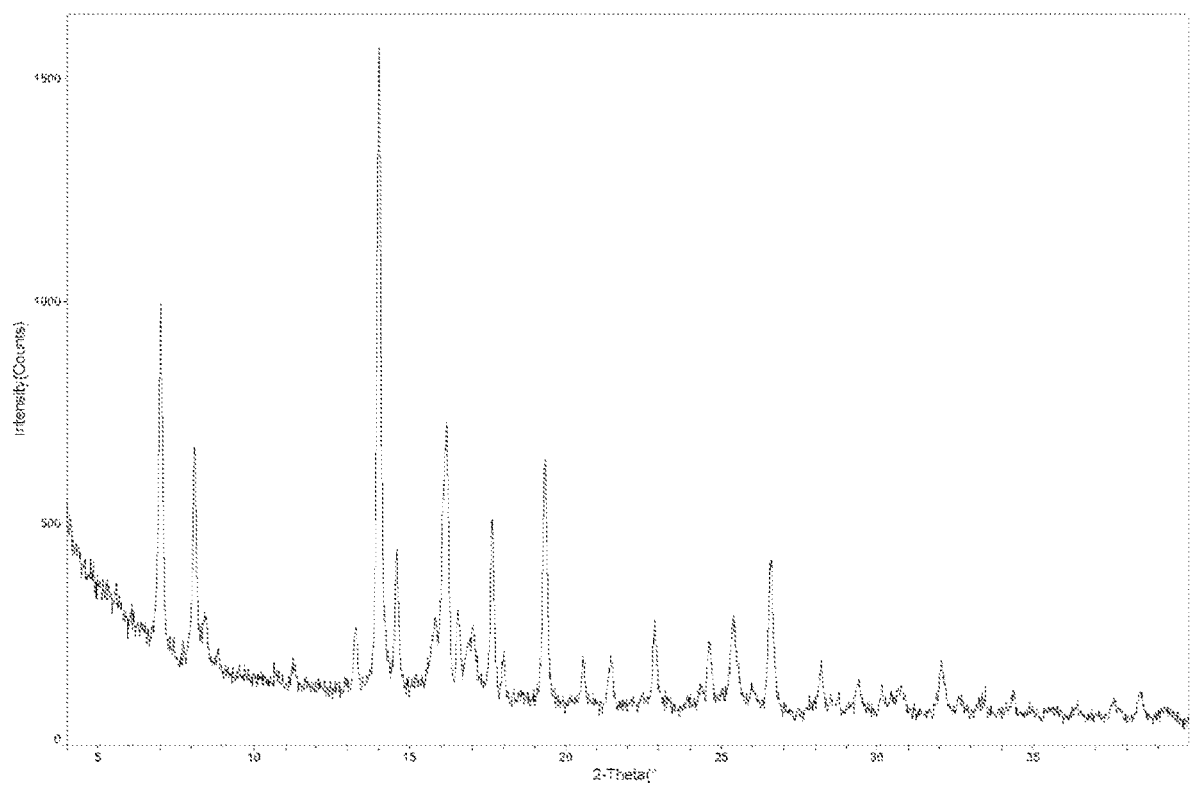
FIG. 16 is an X-ray powder diffraction (XRPD) pattern of crystal VIII of the compound of formula I-A of Example 9.
Figure 17:
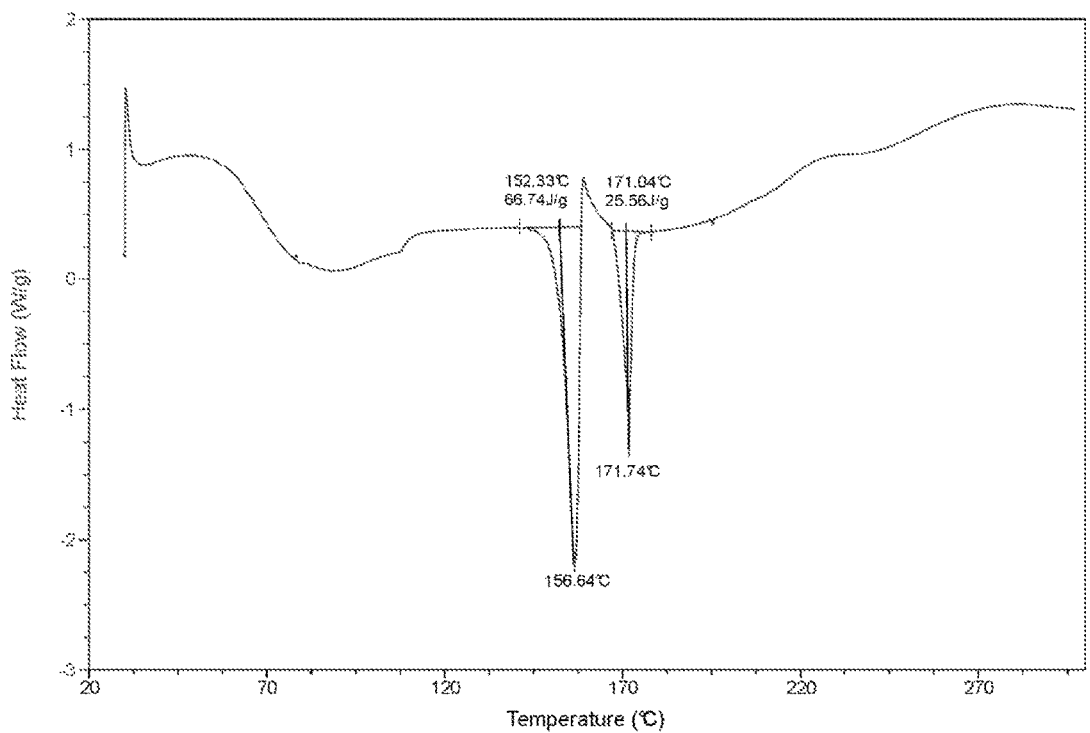
FIG. 17 is a differential scanning calorimetry (DSC) pattern of crystal VIII of the compound of formula I-A of Example 9.
Figure 18:
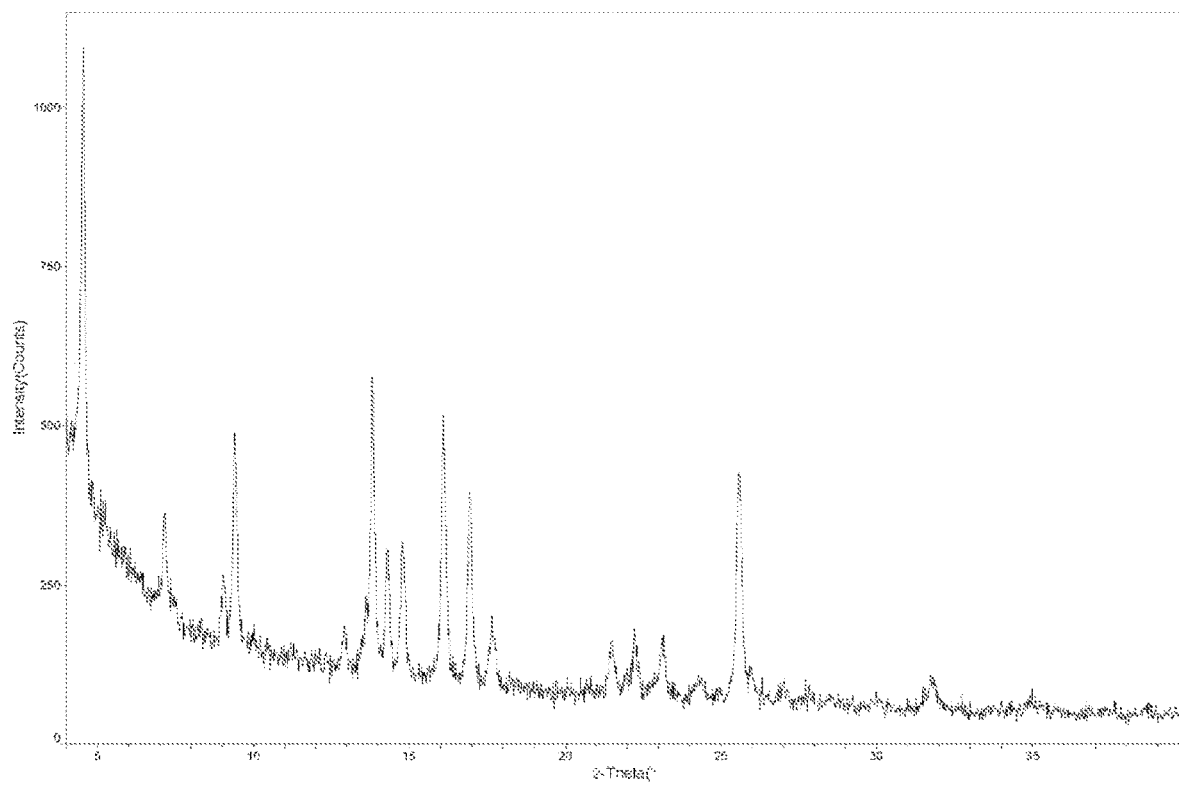
FIG. 18 is an X-ray powder diffraction (XRPD) pattern of crystal IX of the compound of formula I-A of Example 10.
Figure 19:
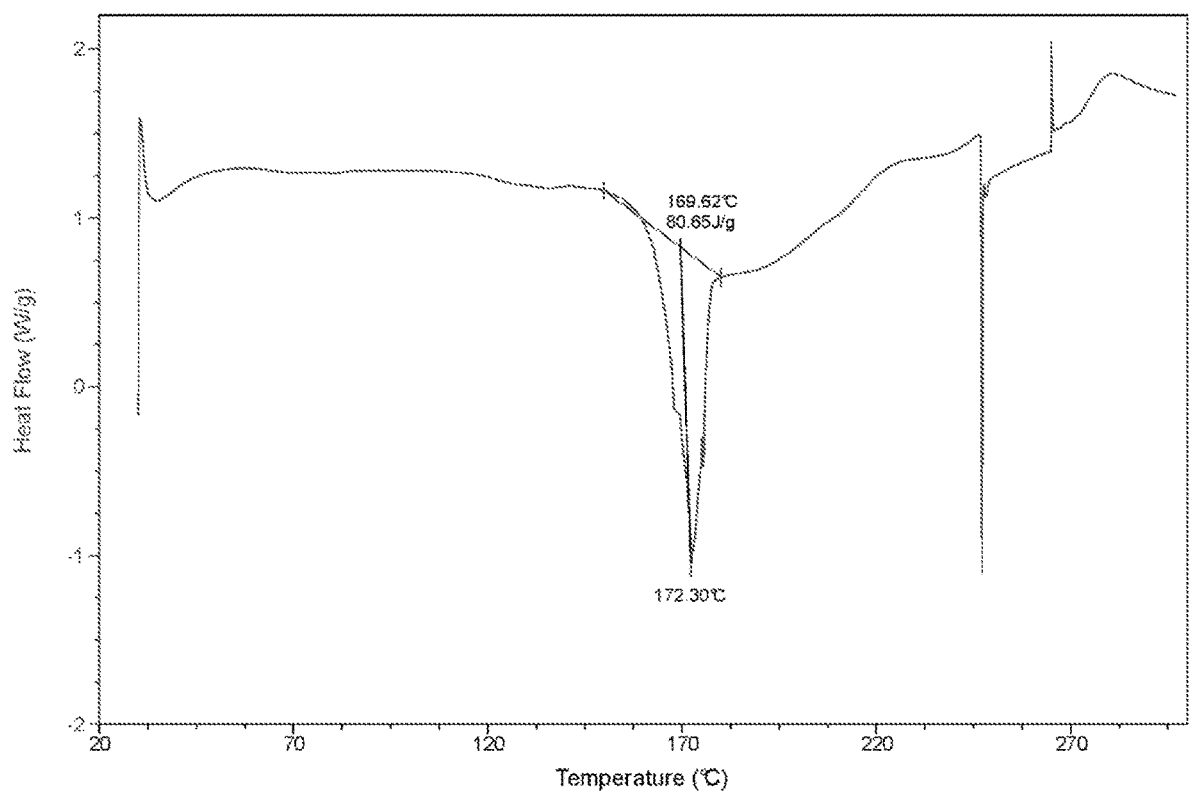
FIG. 19 is a differential scanning calorimetry (DSC) pattern of crystal IX of the compound of formula I-A of Example 10.

The following specific examples are intended to enable persons skilled in the art to understand and implement the present application more clearly. They should not be considered as limitations on the scope of this application, but are merely exemplary explanations and typical representatives of the present application.

All operations involving raw materials that are prone to oxidation or hydrolysis are carried out under the protection of nitrogen. Unless otherwise specified, the raw materials used in the present application are all directly purchased on the market and used without further purification. The solvents used in the present application are all directly purchased on the market and used directly without special treatment. The compounds are named manually or via the ChemDraw® software, and the supplier's catalog names are used for the commercially available compounds.

The following abbreviations are used in the present application: t-BuOK represents potassium tert-butoxide; EtOAc represents ethyl acetate; NaOH represents sodium hydroxide; LiOH.H$_2$O represents lithium hydroxide monohydrate; DMF represents N,N-dimethylformamide; HCl represents hydrogen chloride; T$_3$P represents propylphosphonic anhydride; DIPEA represents N,N-diisopropylethylamine; Boc represents tert-butoxycarbonyl; DEA represents diethanolamine; SFC represents supercritical fluid chromatography; DMSO represents dimethyl sulfoxide; DTT represents dithiothreitol; ddH$_2$O represents deionized water; TFA represents trifluoroacetic acid.

EXAMPLE 1

Preparation of the Compound of Formula I-A

Process 1:

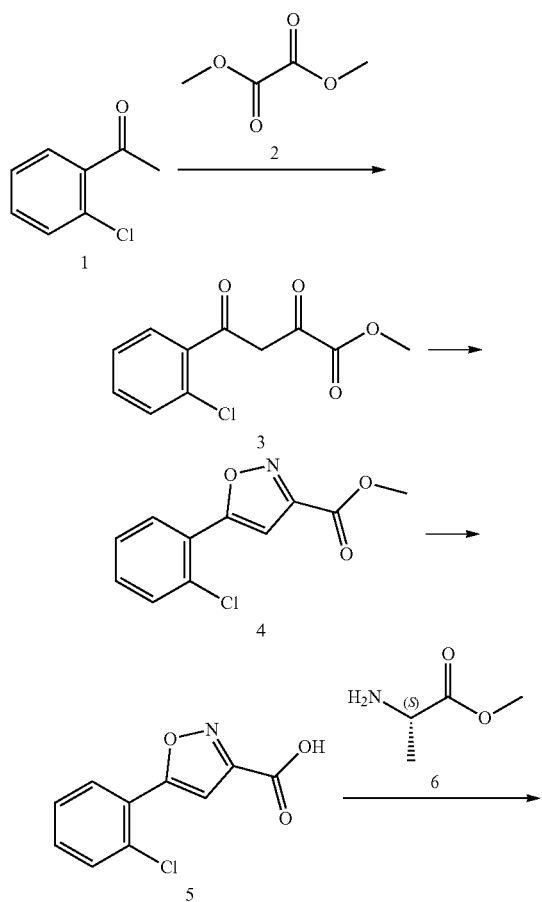

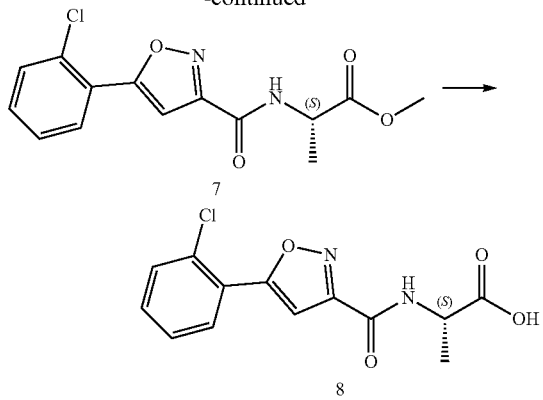

Step 1: Synthesis of Compound 3

Compound 2 (122.22 g) and t-BuOK (145.17 g) were dissolved in tetrahydrofuran (1500 mL), and a mixture of compound 1 (80 g) and tetrahydrofuran (500 mL) was slowly added dropwise to the mixed solution at 0° C. After completion of the addition, the reaction solution was stirred at 20° C. for 2 hours. After completion of the reaction, 1 M of hydrochloric acid aqueous solution was added to the reaction solution and the pH was adjusted to 2-3. After standing for stratification, the water phase was extracted with EtOAc (3 L*2). The organic phases were combined, washed with saturated brine (3 L*3), dried over anhydrous sodium sulfate, and concentrated under reduced pressure to obtain compound 3. The crude product was used directly for the next step without purification.

$^1$H NMR (400 MHz, CDCl$_3$) δ=7.69-7.61 (m, 1H), 7.50-7.37 (m, 3H), 7.01-6.86 (m, 1H), 3.94 (d, J=2.5 Hz, 3H).

Step 2: Synthesis of Compound 4

Compound 3 (446 g) was dissolved in methanol (2000 mL), and then acetic acid (222.60 g) and hydroxylamine hydrochloride (193.19 g) were added thereto. The reaction mixture was stirred at 80° C. for 6 hours. The reaction system was cooled down to room temperature, and water (2000 mL) was added to precipitate solid. It was filtered, and the filter cake was washed with water (1000 mL*3), to give compound 4. The crude product was used directly for the next step without purification.

$^1$H NMR (400 MHz, CDCl$_3$) δ=8.01-7.95 (m, 1H), 7.56-7.50 (m, 1H), 7.45-7.38 (m, 2H), 7.36 (d, J=1.3 Hz, 1H), 4.03 (d, J=0.8 Hz, 3H).

Step 3: Synthesis of Compound 5

Compound 4 (300 g) was dissolved in methanol (2000 mL), then NaOH (4 M, 631.21 mL) was added to the turbid solution, and the solution was gradually became clear. The mixture was stirred at 20° C. for 1 hour, and white solid was formed. 1 M of hydrochloric acid aqueous solution was added to the reaction mixture and the pH was adjusted to 2-3. With constant stirring, the previous white lumpy solid was transformed into a white powdery solid. It was suction-filtered by a Buchner funnel, and the filter cake was washed with water (1000 mL*3), the filter cake was dissolved in ethyl acetate (5 L), dried over anhydrous sodium sulfate, and concentrated under reduced pressure to obtain compound 5. The crude product was used directly for the next step without purification.

$^1$H NMR (400 MHz, DMSO-d$_6$) δ=7.98-7.85 (m, 1H), 7.71-7.44 (m, 3H), 7.34-7.22 (m, 1H).

Step 4: Synthesis of Compound 7

Compound 5 (145.78 g), T₃P (478.70 g, purity 50%) and triethylamine (152.24 g) were dissolved in ethyl acetate (350 mL), and compound 6 (70 g) was added thereto. The reaction solution was stirred at 25° C. for 19 hours, and the reaction system was cooled down to room temperature. Ethyl acetate (200 mL) and water (600 mL) were added to dilute, the organic phase was collected after liquid separation, and the aqueous phase was extracted with ethyl acetate (300 mL*3). The organic phases were combined, washed with 0.5 M of sodium hydroxide solution (500 mL*5) and saturated brine (500 mL*2) successively, dried over anhydrous sodium sulfate, and concentrated under reduced pressure to obtain compound 7.

MS (ESI) m/z: 308.9 [M+H]⁺.

Step 5: Synthesis of Compound 8

Compound 7 (149 g) was dissolved in a mixed solvent of tetrahydrofuran (250 mL) and ethanol (250 mL), and then LiOH.H₂O (101.27 g) and water (250 mL) were added thereto. The reaction solution was stirred at 15° C. for 3 hours. 2 M of hydrochloric acid aqueous solution was added dropwise into the reaction system, the pH was adjusted to 2-3, and a solid was precipitated. It was vacuum filtered using sand core funnel. The filter cake was dissolved in ethyl acetate (2 L), washed with saturated brine (2000 mL*2), dried over anhydrous sodium sulfate, and concentrated under reduced pressure to obtain compound 8.

MS (ESI) m/z: 294.9 [M+H]⁺.

Process 2:

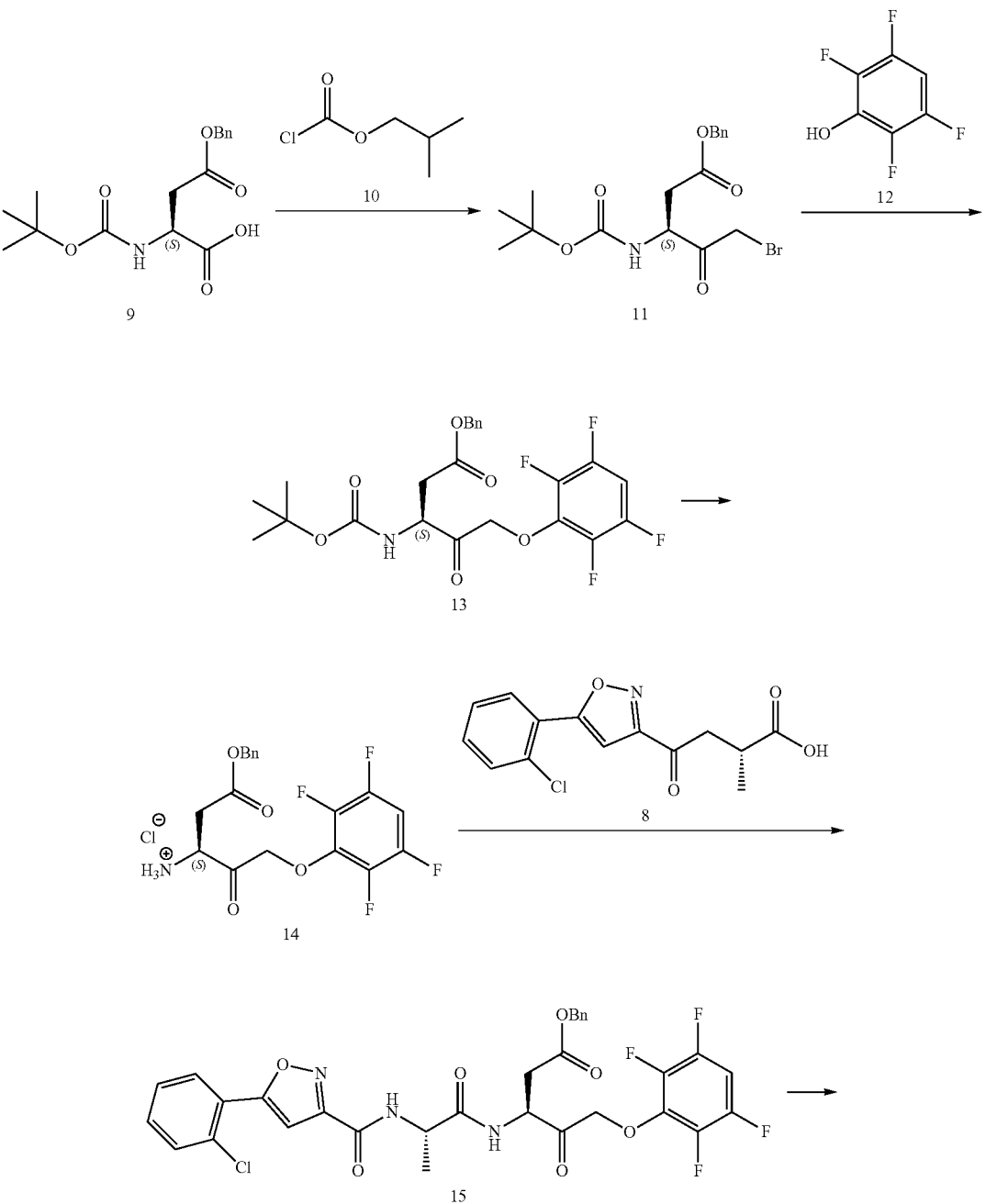

-continued

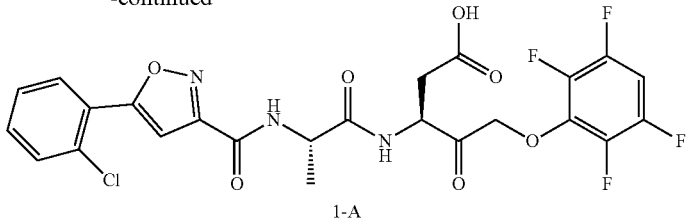

1-A

Step 6: Synthesis of Compound 11

Compound 9 (17.5 g) and 4-methylmorpholine (8.76 g) were dissolved in tetrahydrofuran (200 mL), the solution was cooled down to 0° C. in an ice bath, and compound 10 (11.09 g) was added dropwise thereto, which was stirred for 1 hour while maintaining the temperature at 0° C. The reaction mixture was filtered, the filtrate was poured into a three-necked flask which was pre-cooled in an ice bath, and the filter cake was washed with tetrahydrofuran (pre-cooled in an ice bath, 25 mL). While maintaining the temperature at 0° C., a $CH_2N_2$-ether solution (200 mL) was added into the combined filtrate under the protection of nitrogen, the resultant reaction solution was further stirred at 0° C. for 30 minutes, followed by being heated to 15° C. and stirred for another 2 hours. The reaction mixture was then cooled down to 0° C., and HBr (35% acetic acid solution; 18.77 g, 81.18 mmol, purity 35%) was slowly added thereto. The mixture was stirred at 0° C. for 15 minutes, then heated to 15° C. and continuously stirred for 45 minutes. After completion of the reaction, ethyl acetate (300 mL) and water (250 mL) were added to the reaction solution, which was separated. The organic phase was washed with water (250 mL), saturated sodium bicarbonate solution (250 mL) and saturated saline (250 mL) successively, then dried over anhydrous sodium sulfate, followed by being filtered and concentrated to give compound 11.

MS (ESI) m/z: 301.9 [M-Boc+H]$^+$.

Step 7: Synthesis of Compound 13

Compound 11 (28.06 g) was dissolved in DMF (120 mL), and compound 12 (11.64 g), potassium iodide (1.16 g) and sodium bicarbonate (11.78 g) were added thereto at −5° C. The reaction solution was stirred at −5° C. for 61 hours. Water (250 mL) was added to the reaction solution to quench the reaction, and the mixture was extracted with ethyl acetate (250 mL*2). The organic phases were combined and washed with saturated ammonium chloride solution (200 mL), water (200 mL) and saturated saline (200 mL) in sequence. The organic phase was dried over anhydrous sodium sulfate, filtered and concentrated to give a crude product, which was slurried with petroleum ether/ethyl acetate (10/1) to give compound 13.

$^1$H NMR (400 MHz, DMSO-d$_6$) δ=7.51-7.63 (m, 2H), 7.28-7.40 (m, 5H), 5.26 (br d, J=2.5 Hz, 2H), 5.09 (s, 2H), 4.46 (q, J=7.3 Hz, 1H), 2.86 (brdd, J=6.0, 16.6 Hz, 1H), 2.65 (dd, J=7.5, 16.6 Hz, 1H), 1.38 (s, 9H).

Step 8: Synthesis of Compound 14

Compound 13 (15.70 g) was dissolved in ethyl acetate (34 mL), the system was cooled down in an ice bath, and HCl/ethyl acetate (4 M, 57 mL) was added thereto. The reaction solution was stirred at 0° C. for 1 hour, and the reaction solution was then directly concentrated to give compound 14.

$^1$H NMR (400 MHz, DMSO-d$_6$) δ=8.67 (br s, 3H), 7.63 (tt, J=7.4, 10.8 Hz, 1H), 7.30-7.42 (m, 5H), 5.38 (s, 2H), 5.13 (d, J=1.5 Hz, 2H), 4.50 (br t, J=5.3 Hz, 1H), 3.19 (d, J=5.8 Hz, 2H).

Step 9: Synthesis of Compound 15

Compound 8 (7.03 g) was dissolved in ethyl acetate (185 mL), the system was cooled down to 0° C. in an ice bath, and compound 14 (7.71 g) was added thereto. Then T$_3$P/ethyl acetate (50%, 29.10 g) was added thereto. Finally, DIPEA (9.46 g) was added thereto. The reaction solution was stirred at 20° C. for 1.5 hours. Water (155 mL) and ethyl acetate (155 mL) were added to the reaction solution which was separated. The organic phase was washed with saturated saline (155 mL) twice, and solid was precipitated while washing. It was then filtered and separated. The organic phase was dried over anhydrous sodium sulfate, filtered and concentrated to give a crude product. The filtered solid was combined with the crude product, then successively slurried with n-heptane/ethyl acetate (2/1; 210 mL, stirred at 20° C. for 1 hour), n-heptane/ethyl acetate (2/1; 210 mL, stirred at 20° C. for 13 hours), n-heptane/ethyl acetate (1/1; 100 mL, stirred at 25° C. for 4 hours), and n-heptane/ethyl acetate (1/1; 150 mL, stirred at 25° C. for 14 hours), followed by being filtered to give compound 15.

MS (ESI) m/z: 662.0 [M+H]$^+$

Step 10: Synthesis of Compound I-A

Compound 15 (10.02 g) was dissolved in tetrahydrofuran (400 mL), the system was cooled down in an ice bath, then a solution of LiOH.H$_2$O (761.50 mg) in water (200 mL) was slowly added dropwise at 0° C., and the addition process continued for 40 minutes. After completion of the addition, the reaction solution was further stirred at 0° C. for 5 minutes, and then the reaction solution was adjusted with 1 M of HCl to about pH 1, and extracted with ethyl acetate (400 mL). The organic phase was washed with saturated brine (300 mL), dried over anhydrous sodium sulfate, then filtered and concentrated to give a crude product of compound of formula I-A.

MS (ESI) m/z: 571.9 [M+H]$^+$ $^1$H NMR (400 MHz, DMSO-d$_6$) δ=9.04 (br d, J=6.5 Hz, 1H), 8.67 (br s, 1H), 8.01 (dd, J=2.0, 7.0 Hz, 1H), 7.72-7.80 (m, 1H), 7.54-7.69 (m, 3H), 7.40-7.45 (m, 1H), 5.19 (br s, 2H), 4.64-4.80 (m, 1H), 4.48-4.59 (m, 1H), 2.79-2.88 (m, 1H), 2.72 (br s, 1H), 1.42 (d, J=7.0 Hz, 3H)

EXAMPLE 2

Preparation of Crystal I of the Compound of Formula I-A 8.10 g of the crude compound of formula I-A prepared in Example 1 was added into acetonitrile (300 ml), sonicated, and a white solid was precipitated. Acetonitrile (100 ml) was added thereto, and it was stirred at room temperature for 5 hours and filtered to obtain 4.20 g of white solid. Acetonitrile (40 ml) was added to the solid, stirred at 25° C. for 12 hours, and filtered, and the solvent was drained to give a white solid (3.20 g, 5.60 mmol, purity of chiral SFC: 93.7%, containing 6.3% of the compound of formula I-B), which was crystal I of the compound formula I-A.

Purity analysis method of the chiral SFC: Column signal: Chiralpak AS-3 100×4.6 mm I.D., 3 μm; Mobile phase: (A: $CO_2$; B: ethanol (0.05% DEA)); Gradient: 5%-40% B within 4.5 min, then 40% B for 2 min, and finally 5% B for 1 min; Flow rate: 2.8 mL/min; Column temperature: 40° C.

EXAMPLE 3

Preparation of Crystal II of the Compound of Formula I-A 30.03 mg of crystal I of the compound of formula I-A prepared in Example 2 was weighed and added into a 1.5 mL glass vial, and 1.0 mL of ethanol-water (1:1) was added to form a suspension. After adding a magnetic stir bar, the suspension sample was placed on a magnetic heating stirrer and stirred at 40° C. for two days. After centrifugation, the solid sample was taken, placed in a vacuum drying oven at 30° C. and dried overnight, to obtain crystal II of the compound of formula I-A.

EXAMPLE 4

Preparation of Crystal II of the Compound of Formula I-A 29.97 mg of crystal I of the compound of formula I-A prepared in Example 2 was weighed and added into a 1.5 mL glass vial, 1.0 mL of ethanol was added to form a suspension. After adding a magnetic stir bar, the suspension sample was placed on a magnetic heating stirrer and stirred at 40° C. for two days, and the solution became clear. The glass vial was sealed with tin foil and small holes were made in the foil. The glass vial was placed in a fume hood to volatilize. After about 5 days, solid was precipitated. The solid sample was taken, placed in a vacuum drying oven at 30° C. and dried overnight, to obtain crystal II of the compound of formula I-A.

EXAMPLE 5

Preparation of Crystal IV of the Compound of Formula I-A 29.86 mg of crystal I of the compound of formula I-A prepared in Example 2 was weighed and added into a 1.5 mL glass vial, 1.5 mL of acetone-water (1:2) was added to form a suspension. After adding a magnetic stir bar, the suspension sample was placed on a magnetic heating stirrer and stirred at 40° C. for two days. After centrifugation, the solid sample was taken, placed in a vacuum drying oven at 30° C. and dried overnight, to obtain crystal IV of the compound of formula I-A.

EXAMPLE 6

Preparation of Crystal IV of the Compound of Formula I-A

The crude compound of formula I-A (347 g) prepared in Example 1 was added to a mixed solution of 2.8 L of acetone and 5.6 L of water, and the mixture was stirred at 40-50° C. for 16-48 hours. After filtration, crystal IV of the compound of formula I-A was obtained (308 g, purity of the chiral SFC: 90.34%, chirality test showed that 9.66% of the compound of formula I-B was contained). The purity analysis method of chiral SFC was the same as that in Example 2.

EXAMPLE 7

Preparation of Crystal V of the Compound of Formula I-A 50.01 mg of crystal I of the compound of formula I-A prepared in Example 2 was weighed and added into a 4 mL glass vial, 2 mL of ethanol-water (1:1) was added to form a suspension. After adding a magnetic stir bar, the suspension was placed on a magnetic heating stirrer and stirred at 8° C. for 1 day. After centrifugation, the solid sample was taken, placed in a vacuum drying oven at room temperature and dried overnight, to obtain crystal V of the compound of formula I-A.

EXAMPLE 8

Preparation of Crystal VII of the Compound of Formula I-A 43.13 mg of crystal I of the compound of formula I-A prepared in Example 2 was weighed and added into a 8 mL glass vial, 6 mL of acetone-water (1:2) was added to form a suspension. After adding a magnetic stir bar, it was placed on a magnetic heating stirrer and stirred at 8° C. for 1 day. After centrifugation, the solid sample was taken, placed in a vacuum drying oven at room temperature and dried overnight, to obtain crystal VII of the compound of formula I-A.

EXAMPLE 9

Preparation of Crystal VIII of the Compound of Formula I-A 50.01 mg of crystal I of the compound of formula I-A prepared in Example 2 was weighed and added into a 4 mL glass vial, 2 mL of ethanol-water (1:1) was added to form a suspension. After adding a magnetic stir bar, it was placed on a magnetic heating stirrer and stirred at 8° C. for 6 days. After centrifugation, the solid sample was taken, placed in a vacuum drying oven at room temperature and dried overnight, to obtain crystal VIII of the compound of formula I-A.

EXAMPLE 10

Preparation of Crystal IX of the Compound of Formula I-A 50.15 mg of crystal I of the compound of formula I-A prepared in Example 2 was taken and added into a 4 mL glass vial, 3 mL of acetonitrile was added to form a suspension. After adding a magnetic stir bar, it was placed on a magnetic heating stirrer and stirred at 8° C. for 6 days. After centrifugation, the solid sample was taken, placed in a vacuum drying oven at room temperature and dried overnight, to obtain crystal IX of the compound of formula I-A.

EXAMPLE 11

Preparation of Crystal IX of the Compound of Formula I-A 43.13 mg of crystal I of the compound of formula I-A prepared in Example 2 was weighed and added into a 8 mL glass vial, 6 mL of acetone-water (1:2) was added to form a suspension. After adding a magnetic stir bar, it was placed on a magnetic heating stirrer and stirred at 8° C. for 6 days. After centrifugation, the solid sample was taken, placed in a vacuum drying oven at room temperature and dried overnight, to obtain crystal IX of the compound of formula I-A.

EXPERIMENTAL EXAMPLE 1

Solubility Test of Crystal IV of the Compound of Formula I-A 2 ml of pH medium solutions were transferred into 4 ml glass bottle respectively, and then 8 mg of crystal IV of the compound of formula I-A was added thereto. It was stirred and heated on a magnetic stirrer, and the temperature was kept at 37° C. After 4 hours and 24 hours, 1 mL of sample was taken and centrifuged rapidly, respectively. The pH value of the supernatant was determined, and the supernatant was diluted with diluent. The concentration was determined by HPLC. The results of pH solubility were shown in Table 8.

TABLE 8

Solubilities of crystal IV of the compound of formula I-A in different pH medium solutions

| PH Medium Solution | pH 4 hours | pH 24 hours | Status 4 hours | Status 24 hours | Solubility (mg/mL) 4 hours | Solubility (mg/mL) 24 hours |
|---|---|---|---|---|---|---|
| 0.1N of HCl Buffer | 1.07 | 1.11 | Suspension | Suspension | 0.005 | 0.006 |
| 0.01N of HCl Buffer | 2.01 | 2.07 | Suspension | Suspension | 0.005 | 0.006 |
| pH = 3.8 Buffer | 3.97 | 3.99 | Suspension | Suspension | 0.007 | 0.008 |
| pH = 4.5 Buffer | 4.67 | 4.67 | Suspension | Suspension | 0.016 | 0.016 |
| pH = 5.5 Buffer | 5.55 | 5.55 | Suspension | Suspension | 0.268 | 0.254 |
| pH = 6.0 Buffer | 6.04 | 6.04 | Suspension | Suspension | 0.372 | 0.340 |
| pH = 6.8 Buffer | 6.71 | 6.70 | Suspension | Suspension | 0.775 | 0.702 |
| pH = 7.4 Buffer | 7.28 | 7.24 | Suspension | Suspension | 1.699 | 1.620 |
| Water | 7.83 | 7.34 | Suspension | Suspension | 0.339 | 0.266 |

EXPERIMENTAL EXAMPLE 2

Stability Test of Crystal IV of the Compound of Formula I-A 8 mg of crystal IV of the compound of formula I-A was taken, weighed accurately, placed in the sample vial and spread into a thin layer. The samples at day 0 were sealed with the bottle cap and further sealed with the sealing film, followed by storing in the refrigerator at −20° C. The stability of the samples was tested under 60° C., 92.5% RH, 25° C./60% RH, 40° C./75% RH, 60° C./75% RH and light conditions, respectively.

Analysis method: Agilent 1260 High Performance Liquid Chromatography equipped with DAD detector or Waters 2695 High Performance Liquid Chromatography equipped with PDA detector was used; chromatographic column: Waters Xselect CSH C18 (4.6 mm×150 mm, 3.5 μm), column temperature: 40° C., flow rate: 1.0 ml/min, detection wavelength: 215 nm, injection volume: 10 μL, sample concentration: 0.5 mg/mL, diluent: methanol, and the gradient of mobile phases in Table 9 was used for analysis.

The results of stability test under high temperature and high humidity conditions were shown in Table 10. The results showed that crystal IV of the compound of formula I-A was stable under high temperature and high humidity conditions, the total impurities produced were 0.5% or less, and crystal IV had good druggability.

The results of stability test under different temperatures, humidity and light conditions were shown in Table 11. The results showed that crystal IV of the compound of formula I-A had low hygroscopicity, good stability under high temperature and light conditions, and good druggability.

TABLE 9

Gradient of mobile phases

| Gradient: Time (min) | Mobile Phase A: 0.05% TFA/Water (%) | Mobile Phase B: Methanol (%) |
|---|---|---|
| 0.00 | 60 | 40 |
| 12.00 | 50 | 50 |
| 52.00 | 10 | 90 |
| 55.01 | 60 | 40 |
| 62.00 | 60 | 40 |

TABLE 10

Solid stability test of crystal IV under high temperature and high humidity conditions

| Placement Conditions | Appearance | Crystal | Total Impurities (%) |
|---|---|---|---|
| 25° C./60% RH 10 days | White solid powder | Crystal IV | 0.20% |
| 40° C./75% RH 10 days | White solid powder | Crystal IV | 0.19% |
| 60° C./75% RH 10 days | White solid powder | Crystal IV | 0.48% |

TABLE 11

Stability test results of crystal IV under different temperatures, humidity and light conditions

| Test Item | 0 day (Sealed Storage at −20° C.) (Reference crystal) | 25° C./ 92.5% Relative Humidity (Exposure) | 60° C. (Exposure) | Light |
|---|---|---|---|---|
| Crystal Property | Crystal IV White solid powder | Crystal IV White solid powder | Crystal IV White solid powder | Crystal IV White solid powder |

EXPERIMENTAL EXAMPLE 3

Inhibitory Activity on Caspase In Vitro

Experimental Purpose:
Caspase Inhibitor Screening Kit for BioVision was used in this experiment to test the inhibitory activity of the test compound on Caspase.

Experimental Material:
1) Kit:
Caspase-1 Inhibitor Screening Kit (BioVision #K151-100)
Caspase-3 Inhibitor Screening Kit (BioVision #K153-100)
Caspase-8 Inhibitor Screening Kit (BioVision #K158-100)
Wherein, each caspase enzymatic experiment uses the reagents in corresponding kit thereof. Each enzyme was dissolved in 550 μl of the corresponding 2× reaction buffer, sub-packed and stored at −80° C., respectively.
2) Black 384-well plate (PerkinElmer #6007279)
3) Instrument: Multi-function microplate reader Molecular Devices (Model: SpectraMax M2e)

Experimental Method:
1) The compound of formula I-A was diluted to a 200* test concentration with DMSO via the multiple dilution, then to a 2* test concentration with ddH$_2$O, and added to a 384-well experimental plate at 12.5 μl per well. Test compounds and control compounds were tested at 6 concentration points, test concentrations ranging from 1000 nM to 0.32 nM. The ddH$_2$O containing 1% DMSO was added to the 0% inhibition control well, and a high concentration of the control compound was added to the 100% inhibition control well (final concentration: 5 μM).
2) 2× reaction buffer containing 10 mM DTT was prepared. The enzyme caspase stock solution was diluted 5-fold with 2× reaction buffer containing 10 mM DTT and added to a 384-well experimental plate at 6.25 μl per well. After being mixed, the enzyme and compounds were incubated at 37° C. for 30 minutes.
3) The fluorogenic substrate of the enzyme caspase was diluted 5-fold with 2× reaction buffer containing 10 mM DTT, and then added to a 384-well experimental plate at 6.25 μl per well. The total reaction volume was 25 μl, the final concentration of the substrate was 50 μM, and the final concentration of DMSO was 0.5%. After the substrate was added, the 384-well experimental plate was incubated at 37° C. for 30 minutes.
4) The fluorescence intensity (excitation light wavelength was 400 nm, emission light wavelength was 505 nm) was measured by using a multi-function microplate reader. Fluorescence intensity was used to calculate the inhibitory effect of the compounds on Caspase. GraphPad Prism software was used for fitting compound inhibition curves and calculating IC50 values.

Experimental Results:
The experimental results of the test compound were shown in Table 12.

TABLE 12

| Test result of enzymatic activity of test compound | | | |
|---|---|---|---|
| Compound Number | Caspase-1 | Caspase-3 | Caspase-8 |
| Compound of formula I-A | 4.6 nM | 13.0 nM | 10.3 nM |

What is claimed is:

1. A crystal of a compound of formula I-A:

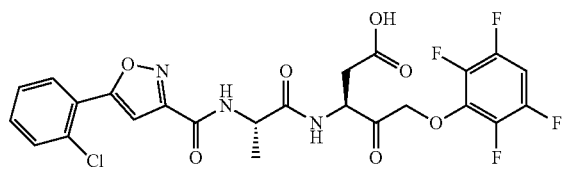

I-A wherein, the crystal is selected from:
crystal IV of the compound of formula I-A, wherein an X-ray powder diffraction spectrum represented by 2θ values has diffraction peaks at about 11.2°, 15.1°, 15.6°, 16.7°, and 25.6°;
crystal I of the compound of formula I-A, wherein an X-ray powder diffraction spectrum represented by 2θ values has diffraction peaks at about 14.0°, 16.3°, 23.0°, and 25.7°;
crystal II of the compound of formula I-A, wherein an X-ray powder diffraction spectrum represented by 2θ values has diffraction peaks at about 8.5°, 14.2°, 15.8°, 17.1°, and 25.5°;
crystal V of the compound of formula I-A, wherein an X-ray powder diffraction spectrum represented by 2θ values has diffraction peaks at about 6.9°, 8.3°, 13.9°, 15.7°, 16.9°, 25.3°, and 32.9°;
crystal VII of the compound of formula I-A, wherein an X-ray powder diffraction spectrum represented by 2θ values has diffraction peaks at about 6.9°, 7.6°, 8.3°, 9.6°, 13.9°, 15.2°, 16.4°, and 16.8°;
crystal VIII of the compound of formula I-A, wherein an X-ray powder diffraction spectrum represented by 2θ values has diffraction peaks at about 7.0°, 8.1°, 14.0°, 16.2°, and 19.3°; or
crystal IX of the compound of formula I-A, wherein an X-ray powder diffraction spectrum represented by 2θ values has diffraction peaks at about 4.6°, 9.4°, 13.8°, 16.1°, 16.9°, and 25.6°.

2. The crystal according to claim 1, wherein the crystal is crystal IV of the compound of formula I-A, and wherein the X-ray powder diffraction spectrum represented by 2θ values has diffraction peaks at about 5.6°, 11.2°, 12.9°, 15.1°, 15.6°, 16.7°, 22.7°, and 25.6°.

3. The crystal according to claim 2, wherein the X-ray powder diffraction spectrum represented by 2θ values has diffraction peaks at about 5.6°, 7.6°, 8.6°, 9.1°, 11.2°, 12.0°, 12.9°, 14.0°, 15.1°, 15.6°, 16.4°, 16.7°, 19.3°, 22.7°, 23.5°, 25.1°, 25.6°, 27.2°, 27.8°, 29.1°, 30.7°, 31.5°, 33.7°, 34.7°, 36.6°, 37.0°, and 38.2°.

4. The crystal according to claim 1, wherein the crystal is crystal IV of the compound of formula I-A, and wherein in a differential scanning calorimetry (DSC) measurement pattern, an onset of absorption peak is at about 167° C.

5. The crystal according to claim 1, wherein the crystal is crystal I of the compound of formula I-A, and wherein the X-ray powder diffraction spectrum represented by 2θ values has diffraction peaks at about 9.6°, 14.0°, 14.5°, 15.0°, 16.3°, 23.0°, 25.1°, and 25.7°.

6. The crystal according to claim 5, wherein the X-ray powder diffraction spectrum represented by 2θ values has diffraction peaks at about 4.7°, 7.4°, 7.9°, 9.6°, 14.0°, 14.5°, 15.0°, 16.3°, 17.1°, 19.8°, 20.4°, 20.9°, 21.7°, 22.5°, 23.0°, 24.5°, 25.1°, 25.7°, 28.1°, 30.0°, 32.0°, 34.1°, 35.2°, and 37.6°.

7. The crystal according to claim 1, wherein the crystal is crystal I of the compound of formula I-A, and wherein in a differential scanning calorimetry (DSC) measurement pattern, onsets of absorption peaks are at about 120° C. and 153° C.

8. The crystal according to claim 1, wherein the crystal is crystal II of the compound of formula I-A, and wherein the X-ray powder diffraction spectrum represented by 2θ values has diffraction peaks at about 5.7°, 8.5°, 14.2°, 15.3°, 15.8°, 17.1°, 20.5°, 20.9°, 22.9°, 23.3°, 24.1°, 25.1°, 25.5°, 26.2°, 26.7°, 28.0°, 29.4°, 30.8°, 33.3°, 35.6°, and 37.1°.

9. The crystal according to claim 1, wherein the crystal is crystal II of the compound of formula I-A, and wherein in a differential scanning calorimetry (DSC) measurement pattern, an onset of absorption peak is at about 147° C.

10. The crystal according to claim 1, wherein the crystal is crystal V of the compound of formula I-A, and wherein the X-ray powder diffraction spectrum represented by 2θ values has diffraction peaks at about 6.9°, 8.0°, 8.3°, 13.9°, 14.5°, 15.1°, 15.7°, 16.9°, 19.2°, 22.8°, 25.3°, and 32.9°.

11. The crystal according to claim 1, wherein the crystal is crystal V of the compound of formula I-A, and wherein in a differential scanning calorimetry (DSC) measurement pattern, onsets of absorption peaks are at about 144° C. and 169° C.

12. The crystal according to claim 1, wherein the crystal is crystal VII of the compound of formula I-A, and wherein the X-ray powder diffraction spectrum represented by 2θ values has diffraction peaks at about 6.9°, 7.6°, 8.3°, 9.6°, 12.4°, 12.7°, 13.9°, 14.6°, 15.2°, 16.4°, 16.8°, 19.2°, 20.5°, 21.9°, 22.3°, 23.1°, 24.8°, 25.6°, 30.5°, 30.9°, and 32.1°.

13. The crystal according to claim 1, wherein the crystal is crystal VII of the compound of formula I-A, and wherein in a differential scanning calorimetry (DSC) measurement pattern, an onset of absorption peak is at about 172° C.

14. The crystal according to claim 1, wherein the crystal is crystal VIII of the compound of formula I-A, and wherein the X-ray powder diffraction spectrum represented by 2θ values has diffraction peaks at about 7.0°, 8.1°, 8.4°, 13.3°, 14.0°, 14.6°, 15.8°, 16.2°, 16.6°, 17.0°, 17.6°, 19.3°, 20.6°, 21.5°, 22.9°, 24.6°, 25.4°, 26.6°, 28.2°, 29.4°, 30.2°, 30.8°, 32.1°, 34.4°, and 38.4°.

15. The crystal according to claim 1, wherein the crystal is crystal VIII of the compound of formula I-A, and wherein in a differential scanning calorimetry (DSC) measurement pattern, onsets of absorption peaks are at about 152° C. and 171° C.

16. The crystal according to claim 1, wherein the crystal is crystal IX of the compound of formula I-A, and wherein the X-ray powder diffraction spectrum represented by 2θ values has diffraction peaks at about 4.6°, 7.2°, 9.0°, 9.4°, 12.9°, 13.8°, 14.3°, 14.8°, 16.1°, 16.9°, 17.7°, 21.5°, 22.2°, 23.2°, 25.6°, and 31.8°.

17. The crystal according to claim 1, wherein the crystal is crystal IX of the compound of formula I-A, and wherein a differential scanning calorimetry (DSC) measurement pattern, an onset of absorption peak is at about 170° C.

18. A pharmaceutical composition, comprising the crystal of the compound of formula I-A according to claim 1.

19. A method for treating a caspase receptor-related disease in a mammal, comprising administering to the mammal in need thereof a therapeutically effective amount of the crystal of the compound of formula I-A according to claim 1.

* * * * *

UNITED STATES PATENT AND TRADEMARK OFFICE
CERTIFICATE OF CORRECTION

PATENT NO. : 11,091,450 B2
APPLICATION NO. : 16/977761
DATED : August 17, 2021
INVENTOR(S) : Songliang Wu Page 1 of 1

It is certified that error appears in the above-identified patent and that said Letters Patent is hereby corrected as shown below:

In the Specification

Column 10, Line 56, delete "20" and insert --2θ--.

Column 11, Line 26, delete "λ," and insert --λ--.

Column 17, Line 55, delete "(brdd," and insert --(br dd,--.

Column 18, Line 34 (Approx.), delete "[M+H]$^+$." and insert --[M+H]$^+$.--.

Column 18, Line 48, delete "[M+H]$^+$." and insert --[M+H]$^+$.--.

Column 18, Line 53, delete "3H)." and insert --3H).--.

Column 21, Line 30, delete "PH" and insert --pH--.

In the Claims

Column 26, Claim 17, Line 24, after "wherein" insert --in--.

Signed and Sealed this
Fifth Day of April, 2022

Drew Hirshfeld
*Performing the Functions and Duties of the
Under Secretary of Commerce for Intellectual Property and
Director of the United States Patent and Trademark Office*